US012747459B2

(12) United States Patent
Avalos et al.

(10) Patent No.: US 12,747,459 B2
(45) Date of Patent: Sep. 29, 2026

(54) SYSTEM AND METHOD FOR INCREASED ALCOHOL TOLERANCE AND PRODUCTION IN YEAST

(71) Applicants: The Trustees of Princeton University, Princeton, NJ (US); Massachusetts Institute of Technology, Cambridge, MA (US); Whitehead Institute for Biomedical Research, Cambridge, MA (US); Kyoto University, Kyoto (JP)

(72) Inventors: José L. Avalos, Princeton, NJ (US); Sarah K. Hammer, Philadelphia, PA (US); Kouichi Kuroda, Kyoto (JP); Gerald R. Fink, Cambridge, MA (US); Gregory Stephanopoulos, Winchester, MA (US)

(73) Assignees: THE TRUSTEES OF PRINCETON UNIVERSITY, Princeton, NJ (US); WHITEHEAD INSTITUTE FOR BIOMEDICAL RESEARCH, Cambridge, MA (US); MASSACHUSETTS INSTITUTE OF TECHNOLOGY, Cambridge, MA (US); KYOTO UNIVERSITY, Kyoto (JP)

( * ) Notice: Subject to any disclaimer, the term of this patent is extended or adjusted under 35 U.S.C. 154(b) by 545 days.

(21) Appl. No.: 17/763,773

(22) PCT Filed: Sep. 25, 2020

(86) PCT No.: PCT/US2020/052619

§ 371 (c)(1),
(2) Date: Mar. 25, 2022

(87) PCT Pub. No.: WO2021/062082

PCT Pub. Date: Apr. 1, 2021

(65) Prior Publication Data

US 2022/0348966 A1 Nov. 3, 2022

Related U.S. Application Data

(60) Provisional application No. 62/905,538, filed on Sep. 25, 2019.

(51) Int. Cl.

| | |
|---|---|
| ***C12P 7/04*** | (2006.01) |
| ***C12N 1/185*** | (2026.01) |
| ***C12N 15/81*** | (2006.01) |
| ***C12P 7/22*** | (2006.01) |
| *C12R 1/865* | (2006.01) |

(52) U.S. Cl.

CPC ................ *C12P 7/04* (2013.01); *C12N 1/185* (2021.05); *C12N 15/81* (2013.01); *C12P 7/22* (2013.01); *C12N 2800/102* (2013.01); *C12R 2001/865* (2021.05)

(58) Field of Classification Search

CPC .. C12N 1/185; C12N 15/81; C12N 2800/102; C12N 15/52; C12R 2001/865; Y02E 50/10; C12P 7/06; C12P 7/16; C12P 7/04; C12P 7/22; C07K 14/395

USPC .......................................................... 436/156

See application file for complete search history.

(56) References Cited

U.S. PATENT DOCUMENTS

| | | | | |
|---|---|---|---|---|
| 9,249,420 | B2 * | 2/2016 | Dundon | C12N 15/81 |
| 2013/0130342 | A1 * | 5/2013 | LaRossa | C12P 7/16 435/254.2 |
| 2013/0288325 | A1 | 10/2013 | Liao et al. | |
| 2016/0108441 | A1 | 4/2016 | Dundon et al. | |

FOREIGN PATENT DOCUMENTS

WO WO-2019148192 A1 * 8/2019 ............. C07K 14/39

OTHER PUBLICATIONS

Oamen, H. P. (2018). Amino acids as a route to biofuel production in *Saccharomyces cerevisiae* (Order No. 10836752). Available from ProQuest Dissertations & Theses Global. (2116957099). https://www.proquest.com/dissertations-theses/amino-acids-as-route-biofuel-production-i/docview/2116957 (Year: 2018).*

Russnak, Roland et al. A Family of Yeast Proteins Mediating Bidirectional Vacuolar Amino Acid Transport, Journal of Biological Chemistry, vol. 276, Issue 26, 23849-23857 (Year: 2001).*

Matsufuji, Y. et al., "Acetaldehyde tolerance in *Saccharomyces cerevisiae* involves the pentose phosphate pathway and oleic acid biosynthesis", Yeast, 2008, 825-833, 25, Wiley InterScience.

Chen, Y. et al.; "Identification and manipulation of a novel locus to improve cell tolerance to short-chain alcohols in *Escherichia coli*", Journal of Industrial Microbiology & Biotechnology, 2017, 589-598, 45.

Crook, N. et al., "Identification of gene knockdown targets conferring enhanced isobutanol and 1-butanol tolerance to *Saccharomyces cerevisiae* using a tunable RNAi screening approach", Applied Genetics and Molecular Biotechnology, 2016, 10005-10018, 100, Springer-Verlag, Germany.

(Continued)

*Primary Examiner* — Robert B Mondesi

(74) *Attorney, Agent, or Firm* — MEAGHER, EMANUEL, LAKS, GOLDBERG & LIAO, LLP

(57) ABSTRACT

A method for producing metabolites that are heavy alcohols, and particularly branched-chain alcohols is provided, involving contacting a suitable substrate with recombinant microorganisms. The microorganisms contain at least one deletion, disruptions, or mutations from the GLN gene family, VPS gene family, GNP gene family, AVT gene family, GCN gene family, or YDR391C, and combinations thereof, and overproduce the heavy alcohol as compared to a wild-type yeast strain.

5 Claims, 17 Drawing Sheets

Specification includes a Sequence Listing.

(56) References Cited

OTHER PUBLICATIONS

Hirasawa, T. et al., "Identification of target genes conferring ethanol stress tolerance to *Saccharomyces cerevisiae* based on DNA microarray data analysis", Journal of Biotechnology, 2007, 34-44, 131, Elsevier.

Grisham, C.M. and Barnett, R.E., "The Effects of Long-Chain Alcohols on Membrane Lipids and The (Na+ + K+)-ATPase", Biochimica et Biophysica Acta, 1973, 417-422, 311, Elsevier Scientific Publishing Company, Netherlands.

Juhnke, Holger et al., "Mutants that show increased sensitivity to hydrogen peroxide reveal an important role for the pentose phosphate pathway in protection of yeast against oxidative stress", Mol Gen Genet, 1996, 456-464, 252, Springer-Verlag, Germany.

International Search Report & Written Opinion for corresponding PCT Application No. PCT/US2020/052619, dated Jan. 13, 2021.

Noda et al., "Reconstruction of metabolic pathway for isobutanol production in *Escherichia coli*", Microbial Cell Factories, vol. 18, Art No. 124, pp. 1-10, Jul. 18, 2019.

* cited by examiner

| Systematic Name | Common Name | Tolerance Factor in 0.6% Isobutanol | Tolerance Factor in 1.2% Isobutanol | Tolerance Factor in 8% EtOH |
|---|---|---|---|---|
| ***YHR183W*** | ***GND1*** | ***0.040*** | ***0.057*** | ***0.309*** |
| ***YNL241C*** | ***ZWF1*** | ***0.090*** | ***0.062*** | ***0.344*** |
| ***YCR024C*** | ***SLM5*** | ***0.105*** | ***0.044*** | ***0.036*** |
| ***YCR028C*** | ***FEN2*** | ***0.130*** | ***0.159*** | ***0.252*** |
| ***YOR332W*** | ***VMA4*** | ***0.174*** | ***0.042*** | ***0.158*** |
| ***YBR171W*** | ***SEC66*** | ***0.205*** | ***0.104*** | ***0.123*** |
| ***YNL064C*** | ***YDJ1*** | ***0.206*** | ***0.102*** | ***0.095*** |
| ***YER122C*** | ***GLO3*** | ***0.228*** | ***0.049*** | ***0.028*** |
| ***YLR240W*** | ***VPS34*** | ***0.231*** | ***0.034*** | ***0.021*** |
| ***YLR304C*** | ***ACO1*** | ***0.316*** | ***0.034*** | ***0.015*** |
| ***YOR036W*** | ***PEP12*** | ***0.326*** | ***0.069*** | ***0.119*** |
| ***YDR323C*** | ***PEP7*** | ***0.370*** | ***0.040*** | ***0.015*** |
| ***YDR495C*** | ***VPS3*** | ***0.377*** | ***0.187*** | ***0.090*** |
| ***YLR447C*** | ***VMA6*** | ***0.403*** | ***0.134*** | ***0.036*** |
| ***YBR030W*** | ***RKM3*** | ***0.403*** | ***0.771*** | ***0.481*** |
| ***YLR244C*** | ***MAP1*** | ***0.424*** | ***0.144*** | ***0.068*** |
| ***YLL028W*** | ***TPO1*** | ***0.425*** | ***0.615*** | ***0.389*** |
| ***YJL129C*** | ***TRK1*** | ***0.433*** | ***0.143*** | ***0.384*** |
| ***YLR138W*** | ***NHA1*** | ***0.437*** | ***0.436*** | ***0.297*** |
| ***YDR207C*** | ***UME6*** | ***0.440*** | ***0.056*** | ***0.086*** |
| ***YDR316W*** | ***OMS1*** | ***0.447*** | ***0.776*** | ***0.431*** |
| ***YCR034W*** | ***ELO2*** | ***0.454*** | ***0.215*** | ***0.119*** |
| ***YDR315C*** | ***IPK1*** | ***0.476*** | ***0.166*** | ***0.258*** |
| ***YFL023W*** | ***BUD27*** | ***0.484*** | ***0.210*** | ***0.172*** |
| ***YDL160C*** | ***DHH1*** | ***0.487*** | ***0.147*** | ***0.170*** |
| YBR018C | GAL7 | 0.513 | 0.376 | 0.118 |
| ***YLR182W*** | ***SWI6*** | ***0.526*** | ***0.093*** | ***0.093*** |
| YEL027W | VMA3 | 0.532 | 0.151 | 0.036 |
| YGL173C | XRN1 | 0.536 | 0.347 | 0.084 |
| YBR173C | UMP1 | 0.537 | 0.196 | 0.149 |
| YHL011C | PRS3 | 0.539 | 0.106 | 0.168 |
| YGL168W | HUR1 | 0.560 | 0.276 | 0.077 |
| YDR417C | - | 0.564 | 0.465 | 0.217 |
| ***YOR035C*** | ***SHE4*** | ***0.573*** | ***0.074*** | ***0.090*** |
| YEL007W | MIT1 | 0.580 | 0.509 | 0.440 |
| YLR396C | VPS33 | 0.580 | 0.113 | 0.058 |
| ***YNL236W*** | ***SIN4*** | ***0.586*** | ***0.028*** | ***0.025*** |
| YHR064C | SSZ1 | 0.586 | 0.263 | 0.101 |
| YBR024W | SCO2 | 0.586 | 0.841 | 0.412 |
| YGL167C | PMR1 | 0.587 | 0.295 | 0.079 |
| YBR105C | VID24 | 0.592 | 0.595 | 0.291 |
| YDL006W | PTC1 | 0.595 | 0.173 | 0.319 |
| YDR320C | SWA2 | 0.596 | 0.514 | 0.176 |
| YOR065W | CYT1 | 0.599 | 0.658 | 0.140 |
| YKL204W | EAP1 | 0.600 | 0.324 | 0.153 |
| ***YGL026C*** | ***TRP5*** | ***0.601*** | ***0.057*** | ***0.258*** |
| YOR304C-A | BIL1 | 0.604 | 0.486 | 0.165 |
| YBR179C | FZO1 | 0.604 | 0.459 | 0.164 |
| YKL212W | SAC1 | 0.606 | 0.211 | 0.172 |
| ***YIL076W*** | ***SEC28*** | ***0.612*** | ***0.044*** | ***0.055*** |
| YER111C | SWI4 | 0.618 | 0.119 | 0.103 |

*FIG. 2A*

| | | | | |
|---|---|---|---|---|
| YMR142C | RPL13B | 0.619 | 0.132 | 0.044 |
| YLR372W | ELO3 | 0.619 | 0.149 | 0.091 |
| YDL182W | LYS20 | 0.621 | 0.152 | 0.368 |
| YGL020C | GET1 | 0.623 | 0.158 | 0.319 |
| ***YOR290C*** | ***SNF2*** | ***0.628*** | ***0.023*** | ***0.066*** |
| YPL060W | MFM1 | 0.633 | 0.589 | 0.489 |
| YGL072C | - | 0.634 | 0.241 | 0.211 |
| YGR257C | MTM1 | 0.644 | 0.244 | 0.398 |
| YGR252W | GCN5 | 0.648 | 0.461 | 0.151 |
| YCL007C | - | 0.650 | 0.148 | 0.091 |
| YBR231C | SWC5 | 0.652 | 0.568 | 0.302 |
| YLR102C | APC9 | 0.657 | 0.724 | 0.735 |
| YDR329C | PEX3 | 0.661 | 0.688 | 0.406 |
| YGR105W | VMA21 | 0.661 | 0.160 | 0.034 |
| ***YDR008C*** | ***-*** | ***0.661*** | ***0.045*** | ***0.183*** |
| YNL171C | - | 0.661 | 0.152 | 0.085 |
| YBL098W | BNA4 | 0.665 | 0.771 | 0.426 |
| ***YER090W*** | ***TRP2*** | ***0.669*** | ***0.038*** | ***0.189*** |
| YDR293C | SSD1 | 0.670 | 0.119 | 0.091 |
| YJR025C | BNA1 | 0.682 | 0.112 | 0.059 |
| YGL152C | - | 0.684 | 0.744 | 0.292 |
| YGR285C | ZUO1 | 0.698 | 0.280 | 0.179 |
| YOR322C | LDB19 | 0.704 | 0.215 | 0.201 |
| YCL023C | - | 0.705 | 0.586 | 0.543 |
| YOR008C | SLG1 | 0.708 | 0.505 | 0.141 |
| YDR484W | VPS52 | 0.713 | 0.156 | 0.118 |
| YKL037W | AIM26 | 0.714 | 0.347 | 0.143 |
| YBR221C | PDB1 | 0.720 | 0.312 | 0.157 |
| YCR020W-B | HTL1 | 0.721 | 0.129 | 0.057 |
| YJL115W | ASF1 | 0.721 | 0.706 | 0.198 |
| YJL127C | SPT10 | 0.723 | 0.802 | 0.378 |
| ***YBR068C*** | ***BAP2*** | ***0.727*** | ***0.096*** | ***0.228*** |
| ***YLR202C*** | ***-*** | ***0.730*** | ***0.041*** | ***0.004*** |
| TOL023W | IFM1 | 0.731 | 0.191 | 0.131 |
| YJL120W | - | 0.731 | 0.182 | 0.370 |
| YKL118W | - | 0.732 | 0.209 | 0.070 |
| YHR067W | HTD2 | 0.736 | 0.159 | 0.135 |
| YPL002C | SNF8 | 0.737 | 0.160 | 0.075 |
| YPR049C | ATG11 | 0.741 | 0.256 | 0.113 |
| YDL172C | - | 0.744 | 0.129 | 0.363 |
| YNL184C | - | 0.747 | 0.425 | 0.154 |
| YBR003W | COQ1 | 0.748 | 0.687 | 0.244 |
| ***YDR127W*** | ***-*** | ***0.748*** | ***0.022*** | ***0.035*** |
| YHR026W | VMA16 | 0.753 | 0.338 | 0.049 |
| YRL001W | DEG1 | 0.754 | 0.637 | 0.337 |
| ***YKL211C*** | ***TRP3*** | ***0.755*** | ***0.071*** | ***0.186*** |
| YLR047C | FRE8 | 0.757 | 0.561 | 0.406 |
| YPL054W | LEE1 | 0.758 | 0.681 | 0.545 |
| YLR358C | - | 0.762 | 0.148 | 0.035 |
| YLR315W | NKP2 | 0.764 | 0.188 | 0.270 |
| YJL056C | ZAP1 | 0.774 | 0.106 | 0.232 |
| YLR337C | VRP1 | 0.775 | 0.442 | 0.137 |
| YMR312W | ELP6 | 0.780 | 0.335 | 0.181 |
| YDR101C | ARX1 | 0.782 | 0.642 | 0.278 |
| YML121W | GTR1 | 0.784 | 0.471 | 0.115 |
| YJL102W | MEF2 | 0.785 | 0.645 | 0.224 |
| YER047C | SAP1 | 0.785 | 0.801 | 0.678 |

*FIG. 2B*

| | | | | |
|---|---|---|---|---|
| | | | | |
| YJR102C | VPS25 | 0.795 | 0.263 | 0.097 |
| ***YPL045W*** | ***VPS16*** | ***0.796*** | ***0.048*** | ***0.021*** |
| YJL189W | RPL39 | 0.800 | 0.336 | 0.203 |
| YGR135W | PRE9 | 0.803 | 0.550 | 0.282 |
| YKL119C | VPH2 | 0.809 | 0.291 | 0.070 |
| YBR006W | UGA2 | 0.816 | 0.826 | 0.519 |
| YJL183W | MNN11 | 0.816 | 0.122 | 0.084 |
| YBR036C | CSG2 | 0.819 | 0.120 | 0.070 |
| YLR399C | BDF1 | 0.824 | 0.291 | 0.091 |
| YNL025C | SSN8 | 0.827 | 0.371 | 0.069 |
| YNL055C | POR1 | 0.830 | 0.154 | 0.109 |
| YLR233C | EST1 | 0.831 | 0.159 | 0.097 |
| YER178W | PDA1 | 0.832 | 0.545 | 0.428 |
| ***YDR078C*** | ***SHU2*** | ***0.850*** | ***0.094*** | ***0.004*** |
| YDL185W | VMA1 | 0.851 | 0.234 | 0.029 |
| ***YGL143C*** | ***MRF1*** | ***0.854*** | ***0.055*** | ***0.013*** |
| YJL180C | ATP12 | 0.854 | 0.620 | 0.250 |
| YKL134C | OCT1 | 0.854 | 0.335 | 0.292 |
| YLR025W | SNF7 | 0.861 | 0.248 | 0.110 |
| YDR354W | TRP4 | 0.863 | 0.143 | 0.365 |
| YDR007W | TRP1 | 0.872 | 0.110 | 0.272 |
| YDL173W | PAR32 | 0.874 | 0.136 | 0.315 |
| YBR212W | NGR1 | 0.877 | 0.745 | 0.533 |
| ***YJL121C*** | ***RPE1*** | ***0.882*** | ***0.080*** | ***0.287*** |
| YLR200W | YKE2 | 0.892 | 0.694 | 0.207 |
| YDL116W | NUP84 | 0.895 | 0.551 | 0.328 |
| YLR382C | NAM2 | 0.895 | 0.483 | 0.190 |
| YJL036W | SNX4 | 0.896 | 0.351 | 0.187 |
| YDR027C | VPS54 | 0.897 | 0.103 | 0.090 |
| YPR160W | GPH1 | 0.898 | 0.382 | 0.088 |
| YOR211C | MGM1 | 0.899 | 0.499 | 0.201 |
| YDR418W | RPL12B | 0.900 | 0.357 | 0.192 |
| YDR018C | - | 0.904 | 0.647 | 0.031 |
| YJL176C | SWI3 | 0.906 | 0.107 | 0.096 |
| YDL118W | - | 0.911 | 0.741 | 0.366 |
| ***YPR060C*** | ***ARO7*** | ***0.913*** | ***0.050*** | ***0.066*** |
| ***YPL040C*** | ***ISM1*** | ***0.920*** | ***0.098*** | ***0.010*** |
| YOR198C | YOR198C | 0.925 | 0.761 | 0.381 |
| YDR193W | - | 0.929 | 0.769 | 0.425 |
| YOR331C | - | 0.931 | 0.366 | 0.062 |
| ***YJR105W*** | ***ADO1*** | ***0.931*** | ***0.071*** | ***0.115*** |
| YJL095W | BCK1 | 0.939 | 0.177 | 0.336 |
| ***YGL148W*** | ***ARO2*** | ***0.942*** | ***0.048*** | ***0.061*** |
| YDR058C | TGL2 | 0.945 | 0.274 | 0.339 |
| YNL315C | ATP11 | 0.956 | 0.417 | 0.259 |
| YPR074C | TKL1 | 0.966 | 0.617 | 0.623 |
| YKR001C | VPS1 | 0.979 | 0.297 | 0.138 |
| YGR163W | GTR2 | 0.982 | 0.544 | 0.159 |
| YOR221C | MCT1 | 0.992 | 0.438 | 0.262 |
| YOL006C | TOP1 | 0.996 | 0.117 | 0.099 |
| YOR070C | GYP1 | 1.011 | 0.397 | 0.299 |
| YOR150W | MRPL23 | 1.013 | 0.736 | 0.291 |
| YDR173C | ARG82 | 1.019 | 0.204 | 0.069 |
| YOL004W | SIN3 | 1.104 | 0.423 | 0.130 |
| ***YDR162C*** | ***NBP2*** | ***1.119*** | ***0.080*** | ***0.166*** |
| YDR184C | ATC1 | 1.247 | 0.885 | 0.441 |

*FIG. 2C*

| Systematic Name | Common Name | Tolerance Factor in 1.5% Isobutanol | Tolerance Factor in 1.6% Isobutanol | Tolerance Factor in 9% EtOH |
|---|---|---|---|---|
| ***YER040W*** | ***GLN3*** | ***0.809*** | ***0.557*** | ***0.267*** |
| ***YJR044C*** | ***VPS55*** | ***0.689*** | ***0.355*** | ***0.464*** |
| ***YDR508C*** | ***GNP1*** | ***0.507*** | ***0.374*** | ***0.401*** |
| ***YKL146W*** | ***AVT3*** | ***0.481*** | ***0.248*** | ***0.037*** |
| ***YKR026C*** | ***GCN3*** | ***0.470*** | ***0.300*** | ***0.003*** |
| ***YDR391C*** | ***-*** | ***0.402*** | ***0.317*** | ***0.408*** |
| YLL039C | UBI4 | 0.391 | 0.251 | 0.128 |
| YGR144W | THI4 | 0.357 | 0.224 | 0.463 |
| YIR005W | IST3 | 0.353 | 0.175 | 0.000 |
| YKR052C | MRS4 | 0.303 | 0.167 | 0.003 |
| YLR278C | - | 0.290 | 0.138 | 0.002 |
| YLR280C | - | 0.286 | 0.159 | 0.002 |
| YOR155C | ISN1 | 0.281 | 0.128 | 0.257 |
| YDR514C | - | 0.280 | 0.166 | 0.315 |
| YKL147C | - | 0.271 | 0.125 | 0.003 |
| YKL051W | SFK1 | 0.253 | 0.132 | 0.323 |
| YGR124W | ASN2 | 0.248 | 0.180 | 0.406 |
| YDR134C | - | 0.242 | 0.131 | 0.337 |
| YDL169C | UGX2 | 0.231 | 0.118 | 0.305 |
| YIL024C | - | 0.231 | 0.159 | 0.148 |
| YLR250W | SSP120 | 0.224 | 0.118 | 0.002 |
| YGR016W | - | 0.222 | 0.142 | 0.330 |
| YLR236C | - | 0.216 | 0.104 | 0.001 |
| YLR279W | - | 0.213 | 0.105 | 0.002 |
| YIL085C | KTR7 | 0.211 | 0.095 | 0.001 |
| YJL201W | ECM25 | 0.207 | 0.122 | 0.297 |
| YPL194W | DDC1 | 0.201 | 0.132 | 0.171 |
| YLR225C | - | 0.188 | 0.230 | 0.397 |
| YPL197C | - | 0.180 | 0.127 | 0.163 |
| YLR445W | GMC2 | 0.170 | 0.100 | 0.003 |
| YLR134W | PDC5 | 0.165 | 0.113 | 0.271 |
| YDR421W | ARO80 | 0.158 | 0.178 | 0.375 |
| YIL088C | AVT7 | 0.154 | 0.124 | 0.159 |
| YDL214C | PRR2 | 0.151 | 0.079 | 0.192 |
| YKL072W | STB6 | 0.150 | 0.090 | 0.194 |
| YML054C | CYB2 | 0.140 | 0.087 | 0.219 |

*FIG. 3*

| GO Term | Cluster Frequency | | Background Frequency | | P-value |
|---|---|---|---|---|---|
| Aromatic amino acid family biosynthetic process | 7 | (4.3%) | 9 | (0.1%) | 7.78E-08 |
| Single-organism cellular process | 98 | (59.8%) | 2626 | (36.7%) | 8.06E-07 |
| Aromatic amino acid family metabolic process | 9 | (5.5%) | 24 | (0.3%) | 1.04E-06 |
| Single-organism process | 107 | (65.2%) | 3031 | (42.3%) | 1.39E-06 |
| Tryptophan biosynthetic process | 5 | (3.0%) | 5 | (0.1%) | 4.58E-06 |
| Indole-containing compound biosynthetic process | 5 | (3.0%) | 5 | (0.1%) | 4.58E-06 |
| Indolalkylamine biosynthetic process | 5 | (3.0%) | 5 | (0.1%) | 4.58E-06 |
| Indole-containing compound metabolic process | 7 | (4.3%) | 14 | (0.2%) | 6.73E-06 |
| Tryptophan metabolic process | 7 | (4.3%) | 14 | (0.2%) | 6.73E-06 |
| Indolalkylamine metabolic process | 7 | (4.3%) | 14 | (0.2%) | 6.73E-06 |
| Vacuolar transport | 19 | (11.6%) | 171 | (2.4%) | 7.24E-06 |
| Cellular monovalent inorganic cation homeostasis | 9 | (5.5%) | 39 | (0.5%) | 0.00013 |
| Cellular chemical homeostasis | 16 | (9.8%) | 148 | (2.1%) | 0.00017 |
| Cellular cation homeostasis | 14 | (8.5%) | 115 | (1.6%) | 0.00023 |
| Cellular biogenic amine metabolic process | 7 | (4.3%) | 22 | (0.3%) | 0.00029 |
| Monovalent inorganic cation homeostasis | 9 | (5.5%) | 43 | (0.6%) | 0.00031 |
| Cellular homeostasis | 17 | (10.4%) | 177 | (2.5%) | 0.00039 |
| Cation homeostasis | 14 | (8.5%) | 123 | (1.7%) | 0.00054 |
| Cellular biogenic amine biosynthetic process | 5 | (8.0%) | 9 | (0.1%) | 0.00054 |
| Amine biosynthetic process | 5 | (8.0%) | 9 | (0.1%) | 0.00054 |
| Cellular amine metabolic process | 8 | (4.9%) | 36 | (0.5%) | 0.00086 |
| Amine metabolic process | 8 | (4.9%) | 36 | (0.5%) | 0.00086 |
| Cellular ion homeostasis | 14 | (8.5%) | 128 | (1.8%) | 0.00087 |
| Small molecule metabolic process | 36 | (22.0%) | 684 | (9.5%) | 0.00098 |
| Chemical homeostasis | 16 | (9.8%) | 170 | (2.4%) | 0.00112 |
| pH reduction | 7 | (4.8%) | 27 | (0.4%) | 0.00136 |
| Intracellular pH reduction | 7 | (4.8%) | 27 | (0.4%) | 0.00136 |
| Vacuolar acidification | 7 | (4.8%) | 27 | (0.4%) | 0.00136 |
| Biological regulation | 63 | (38.4%) | 1604 | (22.4%) | 0.00159 |
| Autophagy | 15 | (9.1%) | 155 | (2.2%) | 0.00172 |
| Inorganic ion homeostasis | 13 | (7.9%) | 118 | (1.6%) | 0.00198 |
| Ion homeostasis | 14 | (8.5%) | 138 | (1.9%) | 0.00217 |
| Regulation of cellular pH | 7 | (4.8%) | 29 | (0.4%) | 0.00229 |
| Regulation of intracellular pH | 7 | (4.8%) | 29 | (0.4%) | 0.00229 |
| Protein localization to vacuole | 13 | (7.9%) | 120 | (1.7%) | 0.00239 |
| Carboxylic acid metabolic process | 23 | (14.0%) | 351 | (4.9%) | 0.00331 |
| Regulation of pH | 7 | (4.8%) | 32 | (0.4%) | 0.00466 |
| Oxoacid metabolic process | 23 | (14.0%) | 365 | (5.1%) | 0.00635 |
| Organic acid metabolic process | 23 | (14.0%) | 365 | (5.1%) | 0.00664 |
| Cellular component organization | 68 | (41.5%) | 1867 | (26.1%) | 0.00781 |

FIG. 4

| Plasmid | Description | Source |
|---|---|---|
| pXP684-GND1 | Overexpression of *GND1* by 2μ *URA3* plasmid containing the endogenous promoter, ORF, and terminator sequence | Huang et al., 2013 |
| pXP684-GND2 | Overexpression of *GND2* by 2μ *URA3* plasmid containing the endogenous promoter, ORF, and terminator sequence | Huang et al., 2013 |
| pXP684-RPE1 | Overexpression of *RPE1* by 2μ *URA3* plasmid containing the endogenous promoter, ORF, and terminator sequence | Huang et al., 2013 |
| pXP684-SOL3 | Overexpression of *SOL3* by 2μ *URA3* plasmid containing the endogenous promoter, ORF, and terminator sequence | Huang et al., 2013 |
| pXP684-TAL1 | Overexpression of *TAL1* by 2μ *URA3* plasmid containing the endogenous promoter, ORF, and terminator sequence | Huang et al., 2013 |
| pXP684-TKL1 | Overexpression of *TKL1* by 2μ *URA3* plasmid containing the endogenous promoter, ORF, and terminator sequence | Huang et al., 2013 |
| pXP684-TKL2 | Overexpression of *TKL2* by 2μ *URA3* plasmid containing the endogenous promoter, ORF, and terminator sequence | Huang et al., 2013 |
| pXP684-ZWF1 | Overexpression of *ZWF1* by 2μ *URA3* plasmid containing the endogenous promoter, ORF, and terminator sequence | Huang et al., 2013 |
| pRS426 | Empty plasmid with 2μ and *URA3* | ATCC: 96099 |
| pJA184 | Isobutanol production by 2μ *URA3* plasmid containing $P_{TDH3}$-*ILV2-HA*-$T_{ADH1}$, $P_{PGK1}$-*ILV3-His*-$T_{CYC1}$, $P_{TEF1}$-*ADH7-Myc*-$T_{ACT1}$, [$P_{TEF1}$-*ILV5-Myc*-$T_{ACT1}$, $P_{TDH3}$-*LlKivD-HA*-$T_{ADH1}$] | Avalos et al., 2013 |
| pYZ84 | Plasmid containing the *lox66-natMX6-lox71* deletion cassette | Hammer and Avalos, 2017 |
| pUG6 | Plasmid containing the *loxP-kanMX4-loxP* deletion cassette | Gueldener et al., 2002 |

* Brackets indicate reverse compliments.

FIG. 12

SYSTEM AND METHOD FOR INCREASED ALCOHOL TOLERANCE AND PRODUCTION IN YEAST

STATEMENT REGARDING FEDERALLY SPONSORED RESEARCH OR DEVELOPMENT

This invention was made with government support under Grant No. DE-SC0019363 and No. 6935036 awarded by the Department of Energy; Grant No. CBET-1751840 and DGE-1656466 awarded by the National Science Foundation; and Grant No. GM035010 awarded by the National Institutes of Health. The government has certain rights in the invention.

CROSS-REFERENCE TO RELATED APPLICATIONS

This invention was made with government support under Grant No. DE-SC0019363 and No. DE-EE0007531 awarded by the Department of Energy; Grant No. CBET-1751840 and DGE-1656466 awarded by the National Science Foundation; and Grant No. GM035010 awarded by the National Institutes of Health. The government has certain rights in the invention.

TECHNICAL FIELD

Recombinant microorganisms and methods of producing such organisms are provided. Also provided are methods of producing metabolites that are alcohols, and particularly branched-chain alcohols, by contacting a suitable substrate with recombinant microorganisms.

SEQUENCE LISTING

A Sequence Listing filed electronically herewith is also hereby incorporated by reference in its entirety (File Name: PRIN-66176_ST25.txt; Date Created: Sep. 21, 2020; File Size: 4,059 bytes.)

BACKGROUND

Concerns about climate change and sustainability have motivated efforts to engineer microbes to convert renewable feedstocks into fuels and chemicals typically derived from petroleum. In order to develop economically competitive production processes for commodity fuels and chemicals, it is critical to obtain the highest yields, titers, and productivities possible. A major barrier to the cost-effective production of microbial fuels and chemicals is the cellular toxicity of the products of interest, which limits the maximum titers that can be achieved. It has been shown that improving microbial tolerance to toxic products can lead to higher production. However, the development of strains with improved tolerance, and potentially increased production, is hampered by the complex and diverse nature of microbial responses to toxic products that leaves many microbial tolerance mechanisms uncharacterized.

Isobutanol and other heavy alcohols, such as isopentanol and 2-methyl-1-butanol, are promising advanced biofuels that could be used as gasoline substitutes, or upgraded to jet fuel. These molecules have superior fuel properties to ethanol, including higher energy density, lower hygroscopicity, and lower volatility that result in increased compatibility with current fuel infrastructure. The yeast *Saccharomyces cerevisiae* is an attractive host for heavy alcohol production because of its facile genetic manipulation, ability to grow at low pH, immunity to phage contamination, and ease of separation. Another key advantage is that *S. cerevisiae* is currently employed in the majority of large-scale bioethanol production processes, which provides an opportunity to simplify and expedite the transition to large-scale production of advanced biofuels by retrofitting existing bioethanol facilities. Furthermore, *S. cerevisiae* has an inherent ability to produce small amounts of heavy alcohols as products of amino acid degradation and may have evolved mechanisms to better tolerate these products. These advantages have motivated efforts to engineer yeast for heavy alcohol production.

Although yeasts such as *S. cerevisiae* are naturally highly tolerant to ethanol, enduring concentrations as high as 18% (v/v), they are still sensitive to ethanol's toxic effects. Previous studies have shown that ethanol primarily affects cell membranes. By increasing membrane fluidity, ethanol decreases membrane integrity and increases ion permeability, perturbing proton homeostasis. Adding potassium, or buffers to limit acidification of the media, increases yeast tolerance to ethanol, boosting ethanol titers. This effect can be reproduced genetically by increasing the activity of TRK1 (a K+ importer) and overexpressing PMA1 (a H+ exporter), indicating that ion homeostasis plays an important role in ethanol sensitivity. Beyond toxicity to the cell membrane, loss of normal vacuolar function or structure can cause increased ethanol sensitivity, implicating protein turnover and ion homeostasis in the ethanol stress response. Lastly, overexpression of genes involved in tryptophan biosynthesis, and genes with binding sites for transcription factors Msn4p/Msn2p, Yap1p, Hsf1p, and Pdr1p/Pdr3p, increase ethanol tolerance.

Considerably less is understood about the mechanisms of toxicity and cell response induced by higher alcohols in yeast. Yet, it is known that butanol isomers are significantly more toxic than ethanol to yeast cells. Similar to ethanol, 1-butanol affects membrane lipid composition and nutrient transport, in addition to inhibiting initiation of translation. However, a tolerance mechanism specific for higher alcohols has been described, in which genes involved in protein degradation are important for cell tolerance to butanol isomers, but not to ethanol. Isobutanol toxicity in yeast is even less understood, with one study revealing that knockdown of the Hsp70 family of heat shock proteins increases isobutanol tolerance. Proteins involved in mitochondrial respiration and glycerol biosynthesis, identified for their ability to increase tolerance to 2-butanol, also appear beneficial for isobutanol tolerance. While data suggests that there are some commonalities in the toxicity responses to different alcohols in *S. cerevisiae* and *Escherichia coli*, response mechanisms in both microbes depend on the chain length and structure of alcohols. Thus, ethanol tolerance cannot be used as an accurate predictor of yeast tolerance to isobutanol or other heavy alcohols.

BRIEF SUMMARY

A first aspect of the present disclosure is a heavy alcohol production system that utilizes an engineered yeast strain having a biosynthetic pathway configured to overproduce at least one heavy alcohol, such as a branched chain alcohol, wherein the engineered yeast strain has at least one disruption of the function of a gene from the GLN gene family, VPS gene family, GNP gene family, AVT gene family, GCN gene family, or YDR391C, and combinations thereof, as compared to a wild-type yeast strain. In some variants, there are multiple disruptions, and in some variants, the disruptions are disruptions of the function of GLN3, VPS55, GNP1, AVT3, GCN3, and/or YDR391C. Optionally, the heavy alcohol is isobutanol, 1-butanol, 2-methyl-1-butanol, 3-methyl-1-butanol, or a combination thereof. Optionally, the engineered yeast strain is *Saccharomyces cerevisiae.*

In some variants, the engineered yeast strain is free of disruptions of the function of tryptophan biosynthesis pathway genes or pentose phosphate pathway (PPP) genes, as compared to a wild-type yeast strain, and in particular, free of disruptions of the functions of genes from the TRP, GND, and/or ZWF gene families.

Optionally, the yeast has been sufficiently modified that the engineered yeast strain has at least a 4-fold increase in the tolerance to the at least one branched chain alcohol over the wild-type yeast strain. Optionally, the yeast has been sufficiently modified that the engineered yeast strain has at least a 5% increase in the production of the at least one heavy alcohol over the wild-type yeast strain, as measured using titers of the at least one branched chain alcohol.

A second aspect of the present disclosure is drawn to a method for producing, or overproducing, at least one heavy alcohol. The method involves providing a heavy alcohol production system as described above, forming a cell culture by fermenting the engineered yeast strain in conditions that enable the expression of the at least one alcohol, and then allowing the engineered yeast strain to produce a larger quantity of the at least one alcohol than can be produced by a wild-type strain. The method may optionally also include producing a filtered supernatant by centrifuging and filtering the cell culture, and optionally analyzing the filtered supernatant to determine the production of the at least one alcohol.

BRIEF DESCRIPTION OF DRAWINGS

FIGS. 2A-2C are the tabulated results of a screen, indicating genes whose deletion leads to sensitivity or hypersensitivity to isobutanol (hypersensitive strains, which have a TF <0.5 in 0.6% isobutanol or TF <0.1 in 1.2% isobutanol, are highlighted in gray). FIG. 2A shows the first 51 strains, FIG. 2B shows the second 57 strains, and FIG. 2C shows the final 56 strains in the screen.

FIG. 3 are the tabulated results of a screen, indicating genes whose deletion confers the highest tolerance to isobutanol (hypertolerant strains, which have a TF >0.4 in 1.5% isobutanol, are highlighted in gray).

FIG. 4 are the tabulated results of the Gene Ontology (GO) enrichment analysis of the 164 genes with the highest isobutanol sensitivity.

FIG. 12 is a table of plasmids used in various embodiments.

DETAILED DESCRIPTION

Figure 1:
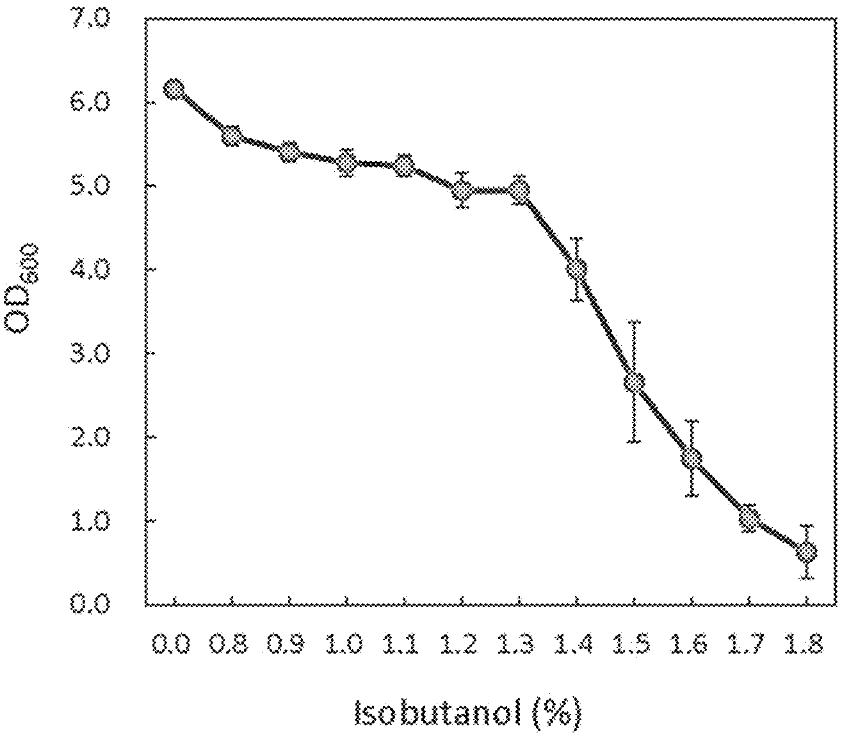
FIG. 1 is a graph of cell growth of the BY4741 wild-type strain in synthetic complete (SC) liquid medium containing various concentrations of isobutanol.

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The term “analog” or “analogous” refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

The term “byproduct” or “by-product” means an undesired product related to the production of a biofuel or biofuel precursor. Byproducts are generally disposed as waste, adding cost to a production process.

The term “deletion” as used herein, refers to the removal of an amino acid within a polypeptide, such as an enzyme. Such removal, i.e., deletion, of one or more amino acids may be done by site-directed mutagenesis or any other method known in the art and by the skilled person.

The term “disruption” as used herein in the context of a gene or a genetic construct encoding a polypeptide means any action at the nucleic acid level that results in; a) a decrease in activity of an encoded polypeptide; b) elimination of the encoded polypeptide activity; c) modification of the encoded polypeptide activity; d) transcription of an incomplete polypeptide sequence; e) incorrect folding of an encoded polypeptide; f) interference with the encoded RNA transcript, or any other activity resulting in a down-regulation or modification of the activity of the gene. A gene may be disrupted, for example, by insertion of a foreign set of base pairs in a coding region, deletion of any portion of the gene, or by the presence of antisense sequences that interfere with transcription or translation of the gene. Disrupted genes are down-regulated. As used herein, the term “down-regulated” refers to a gene that has been mutated, altered, and/or disrupted such that the expression of the gene is less than that associated with the native gene sequence. In another aspect, the term down-regulated may include any mutation that decreases or eliminates the activity of the enzyme encoded by the mutant gene. In another embodiment, down-regulated includes elimination of the gene’s expression (i.e., gene knockout). As used herein, the symbol “A” will be used to denote a mutation in the specified coding sequence and/or promoter wherein at least a portion (up to and including all) of said coding sequence and/or promoter has been disrupted by a deletion, mutation, or insertion. In another embodiment, the disruption can occur by optionally inserting a nucleic acid molecule into the native sequence whereby the expression of the mutated gene is down-regulated (either partially or completely). In yet another embodiment, down-regulation of glycogen synthase expression can occur by down-regulating, altering, or disruption expression of one or more transcription factors influencing expression of the glycogen synthase gene.

Non-limiting examples of techniques one of skill in the art would readily understand how to use in order to disrupt the function of a gene include, but are not limited to, the following: (i) deleting the gene entirely; (ii) adding or subtracting one or more nucleotides causing a frame shift mutation; (iii) introducing a missense mutation, which causes the substitution of a different amino acid in the translated protein, which causes loss or change of function (e.g., loss or reduced catalytic function, loss or gain of binding to another protein, loss or gain of binding to a regulatory molecule, loss or gain of binding to a DNA sequence, inability to be translocated to the correct subcellular compartment, loss or gain of protein stability, etc.); (iv) introducing a non-sense mutation that introduces a stop-codon, which causes early translation termination of the protein encoded by the gene; (v) partial deletion of the gene to remove a functional domain of the protein; (vi) insertion of a sequence of DNA (e.g. a transposon), which impairs the ability to transcribe or translate the gene; and/or (vii) disruption of the promoter sequence (by deletion or mutation), such that the gene is not properly transcribed.

The term “mutation” as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions, i.e., mutations, provided herein are well known in the art.

The term “enzyme” as used herein refers to any substance that catalyzes or promotes one or more chemical or biochemical reactions, which usually includes enzymes totally or partially composed of a polypeptide, but can include enzymes composed of a different molecule including polynucleotides.

The term “gene” refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term “heavy alcohol” as used herein refers to any alcohol containing 3 or more carbons in the carbon chain.

The term “homolog”, used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has “homology” or is “homologous” to a second protein if the nucleic acid sequence that encodes the protein has a similar sequence to the nucleic acid sequence that encodes the second protein. Alternatively, a protein has homology to a second protein if the two proteins have “similar” amino acid sequences. (Thus, the term “homologous proteins” is defined to mean that the two proteins have similar amino acid sequences).

The term “polynucleotide” is used herein interchangeably with the term “nucleic acid” and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "protein," "peptide," or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

The term "reduced activity and/or expression" of an endogenous protein such an enzyme, as used herein and as would be understood by one of ordinary skill in the art, can mean either a reduced specific catalytic activity of the protein (e.g. reduced activity) and/or decreased concentrations of the protein in the cell (e.g. reduced expression), while "deleted activity and/or expression" of an endogenous protein such an enzyme can mean either no or negligible specific catalytic activity of the enzyme (e.g. deleted activity) and/or no or negligible concentrations of the enzyme in the cell (e.g. deleted expression).

The term "substantially free" when used in reference to the presence or absence of enzymatic activities (PDC, GPD, PDH, etc.) in carbon pathways that compete with the desired metabolic pathway (e.g., an isobutanol-producing metabolic pathway) means the level of the enzyme is substantially less than that of the same enzyme in the wild-type host, wherein less than about 50% of the wild-type level is preferred and less than about 30% is more preferred. The activity may be less than about 20%, less than about 10%, less than about 5%, or less than about 1% of wild-type activity.

The term "titer" is defined as the strength of a solution or the concentration of a substance in solution. For example, the titer of a biofuel in a fermentation broth is described as g of biofuel in solution per liter of fermentation broth (g/L).

The term "transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or agrobacterium mediated transformation.

The term "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 g/g would be expressed as 95% of theoretical or 95% theoretical yield.

The disclosed system includes an engineered yeast strain having an increased tolerance to a heavy alcohol, and preferably branched-chain heavy alcohols. Although it is understood in the art that strains identified or engineered for their enhanced tolerance to specific chemicals do not necessarily result in increased production of those chemicals, engineered yeast strains according to the present disclosure will have a biosynthetic pathway configured to overproduce at least one heavy alcohol, and preferably branched-chain heavy alcohols, as compared to a wild-type strain.

It is envisioned that many yeast species could be used to obtain engineered yeast strains according to the invention, for use in the methods of the invention, including both Crabtree-positive and Crabtree-negative species. Suitable yeast species may include, without limitation, *Brettanomyces naardensis, Candida boidinli, Candida guillermondii, Candida intermedia, Candida jefriesii, Candida lyxosophilia, Candida shehatae, Candida tenuis, Debaryomyces hansenii, Dekkera bruxellensis, Enteroramus dimorphus, Hansenula polymorpha, Kluyveromyces fragilis, Kluyveromyces lactis, Kluyveromyces marxianus, Kluyveromyces thermotolerans, Ogataea polymorpha, Pachysolen tannophilus, Pichia segobiensis, Schefersomyces stipitis, Saccharomyces cerevisiae, Spathaspora allomyrinae, Spathaspora boniae, Spathaspora brasiliensis, Spathaspora girioi, Spathaspora passalidarum*, and *Yarrowia lipolytica.*

The engineered yeast strain will have a disruption of the function of one or more genes in the GLN gene family, VPS gene family, GNP gene family, AVT gene family, GCN gene family, or YDR391C, and combinations thereof, as compared to a wild-type yeast strain.

Branched chain alcohols induce a strong nitrogen starvation response mediated by genes in these gene families, such as GLN3 and GCN4, which upregulates amino acid biosynthesis and nitrogen scavenging while downregulating glycolysis, cell wall biogenesis, and membrane lipid biosynthesis, processes important for cell growth. Disruption of the function of genes in those gene families, and preferably disruption of the function of a gene selected from the group consisting of GLN3, VPS55, GNP1, AVT3, GCN3, and YDR391C, generates enhanced tolerance to the branched chain alcohol, and allows for overproduction of the branched chain alcohol as compared to a wild-type strain.

Specific genes from the GLN family include, but are not limited to, GLN1, GLN2, GLN3, and GLN4. Embodiments that disrupt the function of genes from the GLN family preferably include a disruption of the function of GLN3.

Specific genes from the VPS family include, but are not limited to, VPS4, VPS5, VPS13, VPS15, VPS17, VPS20, VPS21. VPS24, VPS27, VPS28, VPS29, VPS30, VPS35, VPS36, VPS38, VPS41, VPS45, VPS51, VPS53, VPS55, VPS60, and VPS61. Embodiments that disrupt the function of the VPS family preferably include a disruption of the function of VPS55.

Specific genes from the GNP family include, but are not limited to, GNP1. Embodiments that disrupt the function of the GNP family preferably include a disruption of the function of GNP1.

Specific genes from the AVT family include, but are not limited to, AVT1, AVT2, AVT3, AVT4, AVT5, AVT6, and AVT7. Embodiments that disrupt the function of the GNP family preferably include a disruption of the function of AVT3.

Specific genes from the GCN family include, but are not limited to, GCN1, GCN2, GCN3, GCN4, and GCN20. Embodiments that disrupt the function of the GCN family preferably include a disruption of the function of GCN3.

In some embodiments, there are one or more disruptions of the function of a gene selected from the group consisting of GLN3, VPS55, GNP1, AVT3, GCN3, and YDR391C.

In some embodiments, there are two or more disruptions of the function of genes from the GLN gene family, VPS gene family, GNP gene family, AVT gene family, GCN gene family, and/or YDR391C. In some embodiments, there are 2 disruptions; 3 disruptions; 4 disruptions; 5 disruptions; or 6 disruptions from those gene families and/or YDR391C gene.

In some embodiments, there are 1 or more, 2 or more, 3 or more, 4 or more, or 5 or more disruptions of a gene selected from the group consisting of GLN3, VPS55, GNP1, AVT3, GCN3, and YDR391C. In some embodiments, GLN3, VPS55, GNP1, AVT3, GCN3, and YDR391C are all disrupted.

In some embodiments, the disruptions include at least a disruption of the function of GLN3 and at least one other disruption of the function of a gene from the GLN gene family, VPS gene family, GNP gene family, AVT gene family, GCN gene family, and/or YDR391C. In some embodiments, the disruptions include at least a disruption of the function of VPS55 and at least one other disruption of the function of a gene from the GLN gene family, VPS gene family, GNP gene family, AVT gene family, GCN gene family, or YDR391C. In some embodiments, the disruptions include at least a disruption of the function of GNP1 and at least one other disruption of the function of a gene from the GLN gene family, VPS gene family, GNP gene family, AVT gene family, GCN gene family, and/or YDR391C. In some embodiments, the disruptions include at least a disruption of the function of AVT3 and at least one other disruption of the function of a gene from the GLN gene family, VPS gene family, GNP gene family, AVT gene family, GCN gene family, and/or YDR391C. In some embodiments, the disruptions include at least a disruption of the function of GCN3 and at least one other disruption of the function of a gene from the GLN gene family, VPS gene family, GNP gene family, AVT gene family, GCN gene family, and/or YDR391C. In some embodiments, the disruptions include at least a disruption of the function of YDR391C and at least one other disruption of the function of a gene from the GLN gene family, VPS gene family, GNP gene family, AVT gene family, and/or GCN gene family. In some embodiments, there are one or more disruptions of a gene selected from the group consisting of GLN3, VPS55, GNP1, AVT3, GCN3, and YDR391C.

In some embodiments, the engineered yeast strain includes a plurality of disruptions of genes where a disruption of the function strain for each of the plurality of disrupted genes has a TF>0.4 at concentrations of the heavy alcohol equal to the $LC_{50}$ of the wild-type strain.

In some embodiments, the engineered yeast strain includes a plurality of disruptions of genes where the disrupted strain has a TF >0.2 at a concentration of the heavy alcohol greater than the $LC_{50}$ of the wild-type strain. For example, if the heavy alcohol is 2-phenylethanol, and the $LC_{50}$ to 2-phenylethanol for the wild-type strain associated with the engineered yeast strain is 0.5%, a deletion strain for a gene according to this embodiment may have a TF of 0.25 in 0.6% 2-phenylethanol.

Optionally, the engineered yeast strain may also include a disruption of the function of at least 1, at least 2, or at least 3 of the following genes: ARO80, ASN2, AVT7, CYB2, DDC1, ECM25, GCM2, ISN1, IST3, KTR7, MRS4, PDC5, PRR2, SFK1, SSP120, STB6, THI4, UBI4, UGX2, YDR134C, YDR514C, YGR016W, YIL024C, YKL147C, YLR225C, YLR236C, YLR278C, YLR279W, YLR280C, and/or YPL197C.

In the most preferred embodiments, the disrupted genes are genes known to be involved in the starvation response by the yeast strain to the presence of the heavy alcohol.

The yeast strains must, necessarily, be capable of producing a heavy alcohol. Preferably, the heavy alcohol contains between 3 and 20 carbons. More preferably, the heavy alcohol contains between 3 and 12 carbons. Still more preferably, the heavy alcohol is a short-chain ($C_4$-$C_9$) alcohol. Although the heavy alcohol may be a polyol, preferably the heavy alcohol contains only a single hydroxyl group. In some embodiments, the heavy alcohol may be primary, secondary, or tertiary alcohol. In some embodiments, the heavy alcohol may be secondary, or tertiary alcohol.

The heavy alcohol may be a straight-chain or branched-chain alcohol. In some preferred embodiments, the carbons in the heavy alcohol do not form a straight-chain alkane. Non-limiting examples of heavy alcohols include: 2-methyl-1-propanol (isobutanol), 2-methyl-1-butanol, 3-methyl-1-butanol (isopentanol), 2-butanol, tert-butanol, 2-phenylethanol, xylitol, or a combination thereof. A skilled artisan will recognize which strains of yeast will have the biochemical pathways necessary to generate a particular heavy alcohol.

Embodiments of the disclosed yeast strains will be configured to overproduce the heavy alcohol. That is, the engineered yeast strains will have an increase in the production of the at least one heavy alcohol over the wild-type yeast strain, as measured using titers of the at least one heavy alcohol. In preferred embodiments, the engineered yeast strains will have an increase in the production of at least 5% over the wild-type yeast strain, as measured using titers of the at least one heavy alcohol. In more preferred embodiments, the engineered yeast strains will have an increase in the production of at least 10% over the wild-type yeast strain, as measured using titers of the at least one heavy alcohol.

Heavy alcohols are typically highly toxic to yeast strains, and it typically does not take much of a heavy alcohol to cause yeast to stop growing and cease production. Isobutanol, for example, is 10 times more toxic for yeast than ethanol. Optionally, the yeast has been sufficiently modified that the engineered yeast strain has a substantial increase in the tolerance to the at least one heavy alcohol over the wild-type yeast strain. In preferred embodiments, the engineered yeast strain has a Tolerance Factor (TF) to the at least one heavy alcohol that is at least 50% greater than the wild-type yeast strain. As an example, if the TF to a heavy alcohol is 0.05 for the wild-type yeast strain, the TF for the engineered yeast strain is at least 0.075. In more preferred embodiments, the engineered yeast strain has a TF to the at least one heavy alcohol that is at least 100% greater than the wild-type yeast strain. The Tolerance Factor (TF) is defined as the ratio of the $OD_{600}$ of cells grown with the heavy alcohol in the medium after 24 h, divided by the $OD_{600}$ of cells grown in the absence of the heavy alcohol for the same amount of time.

In some variants, the engineered yeast strain is free of disruptions of tryptophan biosynthesis pathway genes or pentose phosphate pathway (PPP) genes, as compared to a wild-type yeast strain, and in particular, free of disruptions of the function of genes from the TRP, GND, and/or ZWF gene families. It was found that disruption of the function of genes in these families can cause hypersensitivity to, e.g., isobutanol and other heavy alcohols, but not ethanol. In particular, disruptions of TRP2, TRP3, TRP5, GND1, and ZWF1 are preferably avoided.

In some embodiments, the engineered strain is free of disruption of the function of at least one gene selected from ACO1, ADO1, ARO2, ARO7, BAP2, BUD27, DHH1, ELO2, FEN2, GLO3, GND1, IPK1, ISM1, MAP1, MRF1, NBP2, NHA1, OMS1, PEP12, PEP7, RKM3, RPE1, SEC28, SEC66, SHE4, SHU2, SIN4, SLM5, SNF2, SWI6, TPO1, TRK1, TRP2, TRP3, TRP5, TYLR202C, UME6, VMA4, VMA6, VPS16, VPS3, VPS34, YDJ1, YDR008C, YDR127W, and ZWF1. In preferred embodiments, the strain is free of disruption of the function of at least 10, at least 20, or at least 30 of those genes. In more preferred embodiments, the strain is free of disruption of the function of at least 40 of those genes. In the most preferred embodiments, the strain is free of disruption of the function of all of the listed genes.

A second aspect of the present disclosure is drawn to a method for producing, or overproducing, at least one heavy alcohol. The method involves providing an embodiment of an engineered yeast strain as described above for use in a heavy alcohol production system. In preferred embodiments, the engineered yeast strain will be added to a bioreactor.

A cell culture will then be formed by fermenting the engineered yeast strain in conditions that enable the expression of the at least one heavy alcohol. These conditions will be known to those of skill in the art, and will depend, in part, on the particular strain of yeast involved. Typically, this will require at least providing an appropriate fermentation medium for the engineered yeast strain (such as a commercially-available liquid synthetic complete (SC) media) and fermenting at an appropriate temperature (such as between 30° C. and 40° C., depending upon species), and optionally using agitation, under anaerobic or semi-aerobic conditions, such that the engineered yeast strain will begin producing the heavy alcohol.

The method then requires that the yeast strain be allowed to ferment and overproduce the heavy alcohol(s) as compared to what would have been produced using a wild-type strain.

In some embodiments, the method also includes producing a filtered supernatant by separating (such as via sedimentation, and/or centrifuging) and/or filtering the cell culture. In some embodiments, the method also includes analyzing the filtered supernatant to determine and/or quantify the production of the at least one heavy alcohol.

Example 1: Estimating $LC_{50}$ for Isobutanol in Liquid and Solid Media

A first example is for the identification of the $LC_{50}$ (lethal concentration for 50% of cells) of isobutanol for the BY4741 wild type strain of *S. cerevisiae*, the strain from which a gene deletion library was developed (Giaever et al., 2002; Winzeler et al., 1999). Identifying the $LC_{50}$ is useful, as screening the gene deletion library using a heavy alcohol concentration near the $LC_{50}$ ensures that the concentration is high enough to probe changes in the heavy alcohol (here, isobutanol) tolerance across different strains in the collection, but below the concentration that would be lethal to all deletion strains. The cell growth of BY4741 in synthetic complete (SC) liquid medium containing concentrations of isobutanol ranging from 0.0% to 1.8% (v/v) was monitored by measuring the optical density at 600 nm ($OD_{600}$) after 24-h cultivation. As shown in FIG. 1, cell growth was marginally affected at concentrations below 1.3% but was significantly inhibited at those above 1.6%. Isobutanol concentrations of 1.4% and 1.5% caused moderate inhibition, with 1.5% isobutanol reducing wild type growth by slightly more than half, thereby approximating the $LC_{50}$.

To evaluate isobutanol growth inhibition on solid medium, serial dilutions of BY4741 were spotted onto SC agar plates containing 0.0% to 3.0% isobutanol. On agar plates containing 2.4% isobutanol, cell growth is still observable but noticeably inhibited. The higher $LC_{50}$ determined from agar plates may be the result of higher cell tolerance to isobutanol in solid media; however, it could also reflect the difficulty in accurately preparing solid media with specific isobutanol concentrations due to isobutanol evaporation during the pouring of hot agar.

Example 2: Screen for Deletion Strains with Increased Sensitivity or Tolerance to Isobutanol Utilizing the LC50 results, one can screen a gene deletion library (here, the BY4741 library [Giaever et al., 2002; Winzeler et al., 1999]) for changes in cell growth in liquid SC medium containing the heavy alcohol at an amount that is 0.1% or 0.2% (v/v) less than the LC50. Here, 1.4% (v/v) isobutanol was used. At this conservative concentration (slightly lower than the apparent LC50), one is able to identify gene deletion strains with increased sensitivity or tolerance to isobutanol relative to wild type. To quantify these phenotypes, a tolerance factor (TF) was defined as the ratio of the OD600 of cells grown with isobutanol in the medium after 24 h, divided by the OD600 of cells grown in the absence of isobutanol for the same amount of time. Thus, one can classify deletion strains as having increased sensitivity or tolerance to isobutanol based on the comparison of their TF values to that of the wild type strain in, e.g., 1.4% isobutanol measured during the screen. This initial screen identified 1025 strains with 7 increased sensitivity (TF<0.2) and 517 strains with enhanced tolerance (TF >0.8). The 1542 strains with TF<0.2 or TF >0.8 identified in the initial screen were subjected to a second screen to find those with hypersensitivity or hypertolerance to isobutanol. The 1025 sensitive strains were grown in lower isobutanol concentrations (1.2% and 0.6%) to identify those exhibiting significant growth inhibition even at reduced isobutanol concentrations. This screen was repeated for the 164 most sensitive strains identified in the second screen (See FIGS. 2A-2C). In a similar manner, the 517 tolerant strains were grown in higher concentrations of isobutanol (1.5% and 1.6%) to identify the most tolerant strains. This screen was repeated for the 36 most tolerant strains identified in the second screen (See FIG. 3). To assess the specificity of changes in tolerance to isobutanol, the growth of these selected strains in media containing ethanol can also be measured: 8% for sensitive strains or 9% for tolerant strains.

Out of the 164 sensitive strains, the 46 strains that continue to display increased sensitivity to isobutanol at lower concentrations (TF<0.5 in 0.6% isobutanol or TF<0.1 in 1.2% isobutanol) can be categorized as hypersensitive. These strains are highlighted in gray in FIGS. 2A-2C. Among the 36 strains with increased tolerance, 6 continue to display increased tolerance (TF >0.4) in 1.5% isobutanol, which we categorize as hypertolerant (FIG. 3).

Next, a Gene Ontology (GO) enrichment analysis of genes deleted in the 164 most sensitive and 36 most tolerant strains can be performed. Although genes deleted in strains with enhanced tolerance are not enriched in any specific GO term, we found that gene deletions in strains with increased sensitivity are enriched in several biological processes, including 8 aromatic amino acid-related processes, cellular ion homeostasis, and vacuolar functions (See FIG. 4). In fact, five strains harboring deletions in the TRP gene family, encoding enzymes in tryptophan biosynthesis, show increased isobutanol sensitivity (with trp2Δ, trp3Δ, and trp5Δ being hypersensitive strains). One can examine the increased sensitivity to isobutanol caused by TRP1 deletion because it is an auxotrophic marker in commonly used strains, such as CEN.PK- and SEY6210-derived strains. These strains exhibit increased isobutanol sensitivity similar to that of the BY4741 trp1Δ strain in 1.3% isobutanol. Furthermore, after repairing the TRP1 allele in CEN.PK2-1C and SEY6210, wild-type (BY4741) levels of isobutanol tolerance are recovered. These results suggest that tryptophan biosynthesis is important for heavy alcohol stress response.

Example 3: Hypersensitive Strains Demonstrate Specific Sensitivity to Isobutanol and Other C4-C6 Alcohols Growth of 19 hypersensitive strains was measured in liquid SC medium containing 0.6%, 1.0%, or 1.4% isobutanol, or 8% ethanol. These growth experiments were initiated at an OD600 of 0.1, unlike in previous screens, which started with much smaller inoculums (from a 96-pin replicator). In 1.4% isobutanol, growth of all 19 strains is strongly inhibited compared to the wild type BY4741 strain. However, in media containing 0.6% or 1.0% isobutanol, the sensitivity varies between strains. Four strains—gnd1Δ, zwf1Δ, vps34Δ, and pep12Δ—display TF values less than 0.3 even in 0.6% isobutanol. Among them, the gnd1Δ and zwf1Δ deletion strains show the greatest sensitivity.

Figure 5:
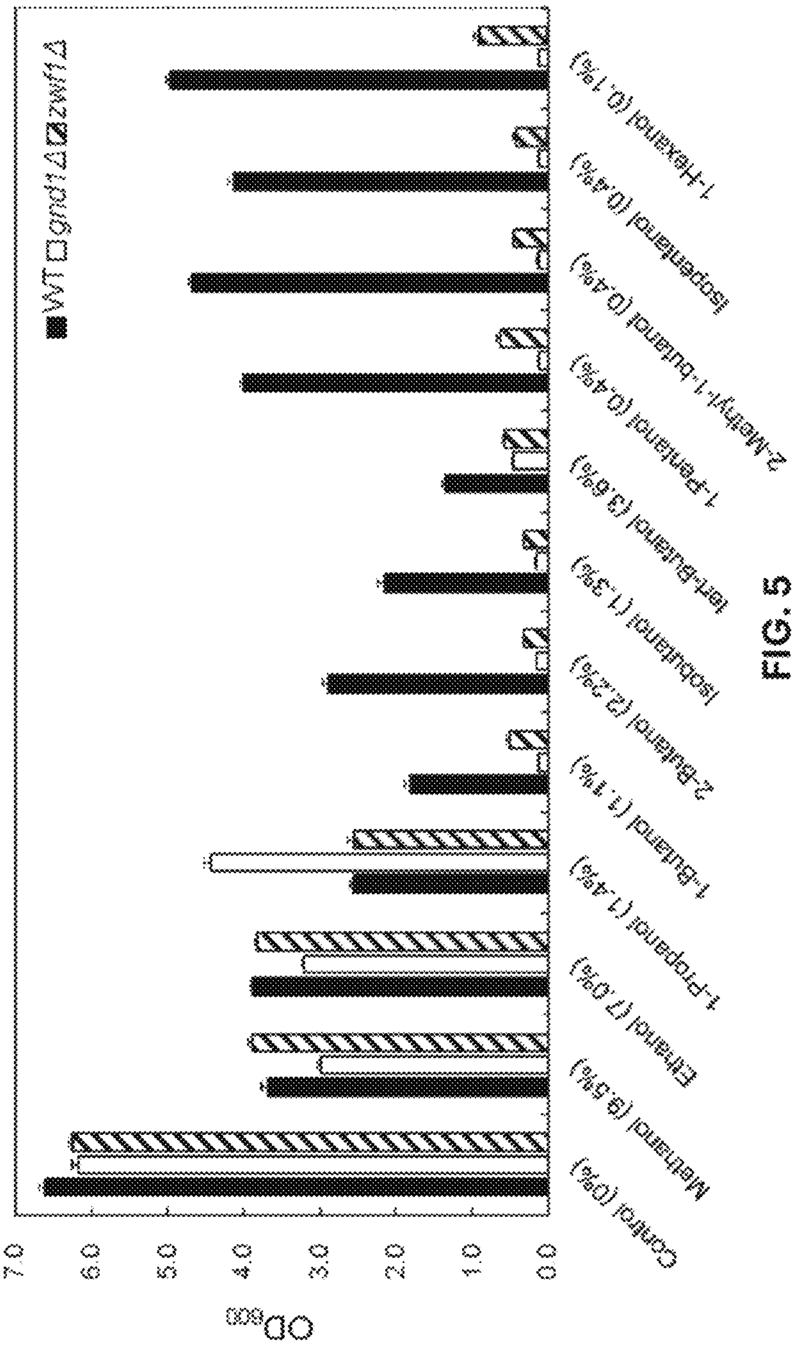
FIG. 5 is a graph illustrating cell growth of wild-type, gnd1Δ and zwf1Δ strains in the presence of various alcohols.

Among the hypersensitive strains, gnd1Δ, zwf1Δ, and nha1Δ have a unique phenotype: despite their hypersensitivity to isobutanol, they are no more sensitive to ethanol than the wild type strain. In contrast, the other hypersensitive strains also have increased sensitivity to 8% ethanol. Thus, deletion of GND1, ZWF1, or NHA1 causes heavy alcohol hypersensitivity in both liquid and solid media. It was confirmed that the isobutanol-specific hypersensitivity observed in the two most sensitive strains—gnd1Δ and zwf1Δ—is due to loss of GND1 and ZWF1 function, respectively, by reconstructing GND1 and ZWF1 gene deletions in the wild type BY4741 strain. The sensitivity of gnd1Δ and zwf1Δ strains to other alcohols including methanol, 1-propanol, 1-butanol, 2-butanol, tert-butanol, 1-pentanol, 2-methyl-1-butanol, isopentanol, and 1-hexanol was explored. As seen in FIG. 5, neither strain demonstrates significantly increased sensitivity to methanol, ethanol, or 1-propanol compared to the wild type strain. However, cell growth is substantially inhibited in the presence of all alcohols tested with four or more carbons. These results indicate that GND1 and ZWF1 play crucial roles in cellular tolerance to at least $C_4$-$C_6$ alcohols, regardless of their branching. However, neither deletion of GND1 nor ZWF1 appears to affect ethanol tolerance.

Figure 6:
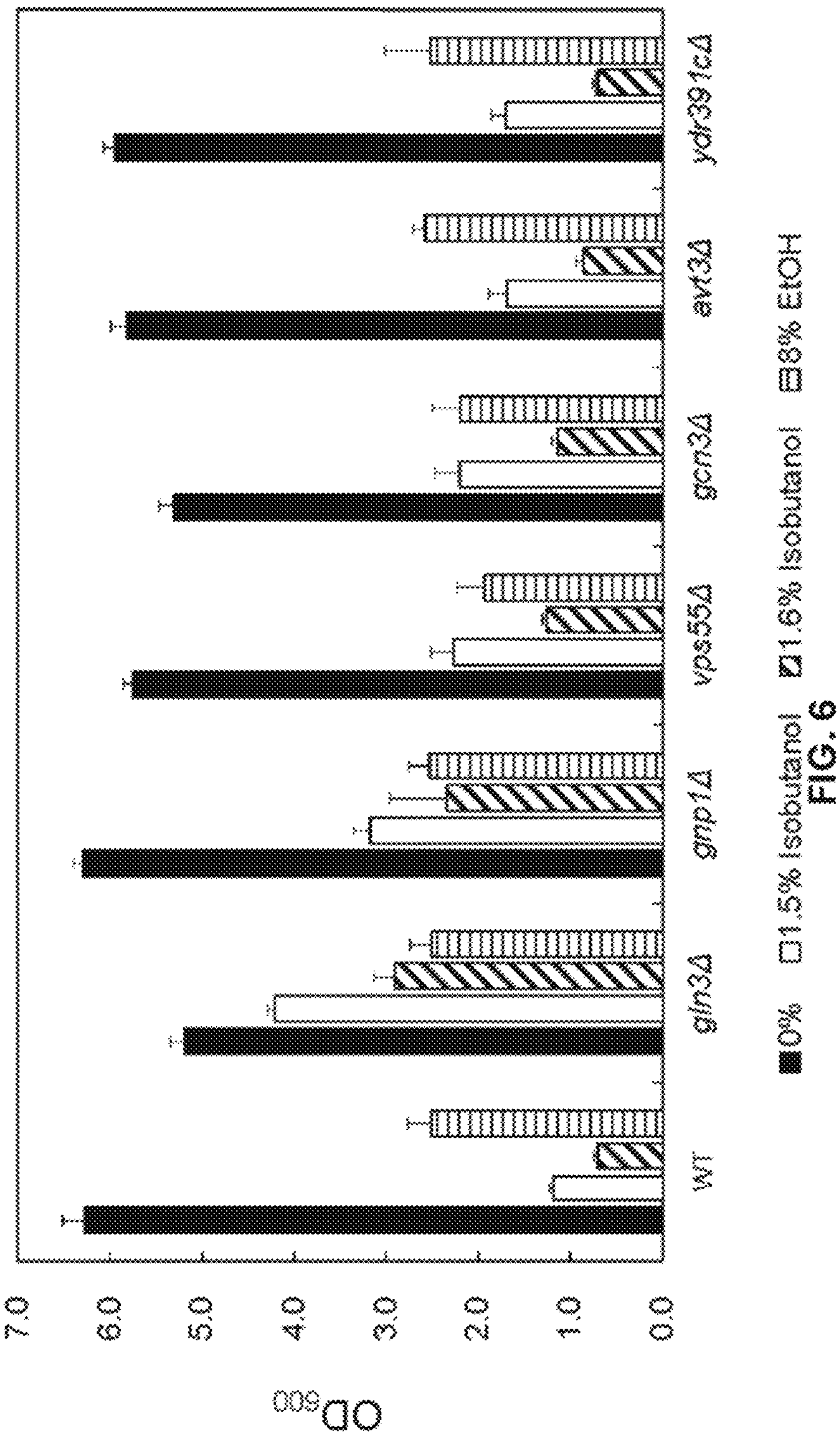
FIG. 6 is a graph showing isobutanol and ethanol tolerance of six hypertolerant strains.

Example 4: Deletion of GLN3 Enhances Yeast Tolerance Specifically to Branched-Chain Alcohols The six hypertolerant strains were examined in liquid medium containing heavy alcohols. In this example, the liquid medium contained 1.5% or 1.6% isobutanol, or 8% ethanol. As shown in FIG. 6, these deletion strains—gln3Δ, gnp1Δ, vps55Δ, gcn3Δ, avt3Δ, and ydr391cΔ—grow better than the wild type in 1.5% isobutanol; gln3Δ, gnp1Δ, vps55Δ, and gcn3Δ also demonstrate enhanced tolerance in 1.6% isobutanol. Notably, all six hypertolerant deletion strains are at least as sensitive to 8% ethanol as the wild type strain.

The gln3Δ strain can grow on SC agar medium containing 2.7% isobutanol. As in liquid medium, the enhanced tolerance of these strains to isobutanol does not translate into enhanced tolerance to ethanol in solid medium. The results show that deletion of GLN3 confers the highest tolerance to heavy alcohols in liquid and solid medium, with $OD_{600}$ values more than three times those of the wild type strain in liquid medium.

GLN3 encodes a transcriptional activator that, in response to nitrogen deprivation, induces the expression of genes that are subjected to nitrogen catabolite repression in the presence of high-quality nitrogen sources (Courchesne and Magasanik, 1988; Magasanik and Kaiser, 2002). It was confirmed that the heavy alcohol-specific hypertolerance of the gln3Δ strain was due to loss of the GLN3 gene by reconstructing GLN3 deletions in the parent CEN.PK2-1C (with TRP1 restored) and BY4741 strains.

Figure 7:
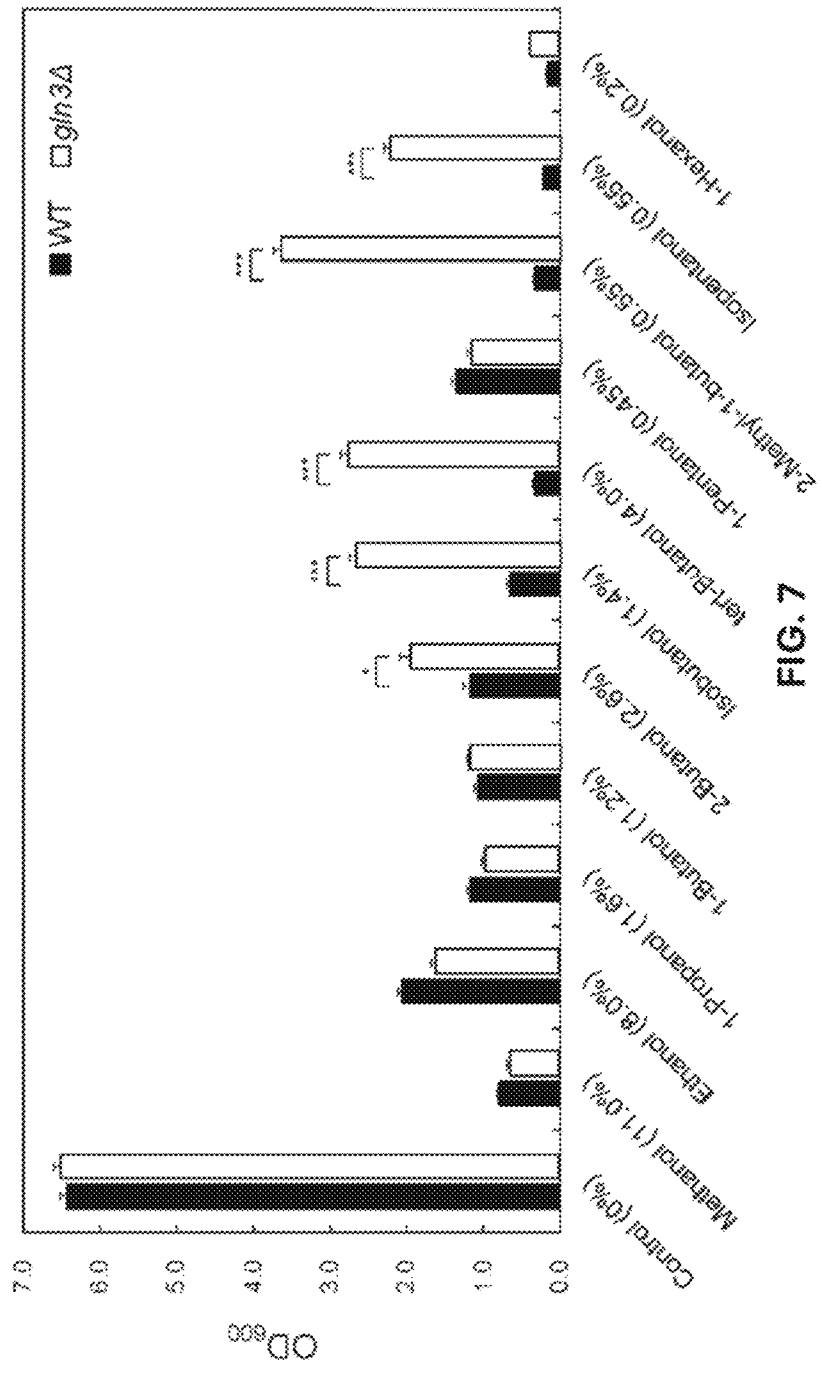
FIG. 7 is a graph showing tolerance of a gln3Δ strain to various alcohols in liquid medium.

Tolerance of the gln3Δ strain to other alcohols was explored by measuring its growth in liquid medium containing methanol, 1-propanol, 1-butanol, 2-butanol, tert-butanol, 1-pentanol, 2-methyl-1-butanol, isopentanol, or 1-hexanol. As seen in FIG. 7, compared to the wild type strain, the gln3Δ strain has dramatically enhanced tolerance to branched-chain alcohols (isobutanol, tert-butanol, 2-methyl-1-butanol, and isopentanol), with an $OD_{600}$ as much as 11.4-fold higher in the presence of 0.55% 2-methyl-1-butanol. A smaller, but statistically significant, increase in tolerance is observed in the presence of the linear secondary alcohol, 2-butanol. However, the gln3Δ strain does not statistically increase tolerance to the linear primary alcohols 1-propanol, 1-butanol, 1-pentanol, 1-hexanol, or the short-chain alcohols methanol and ethanol; in fact, the gln3Δ strain is more sensitive to some of these alcohols than the wild type strain. Therefore, deletion of GLN3 confers enhanced tolerance specifically to branched-chain heavy alcohols.

Figure 8A:
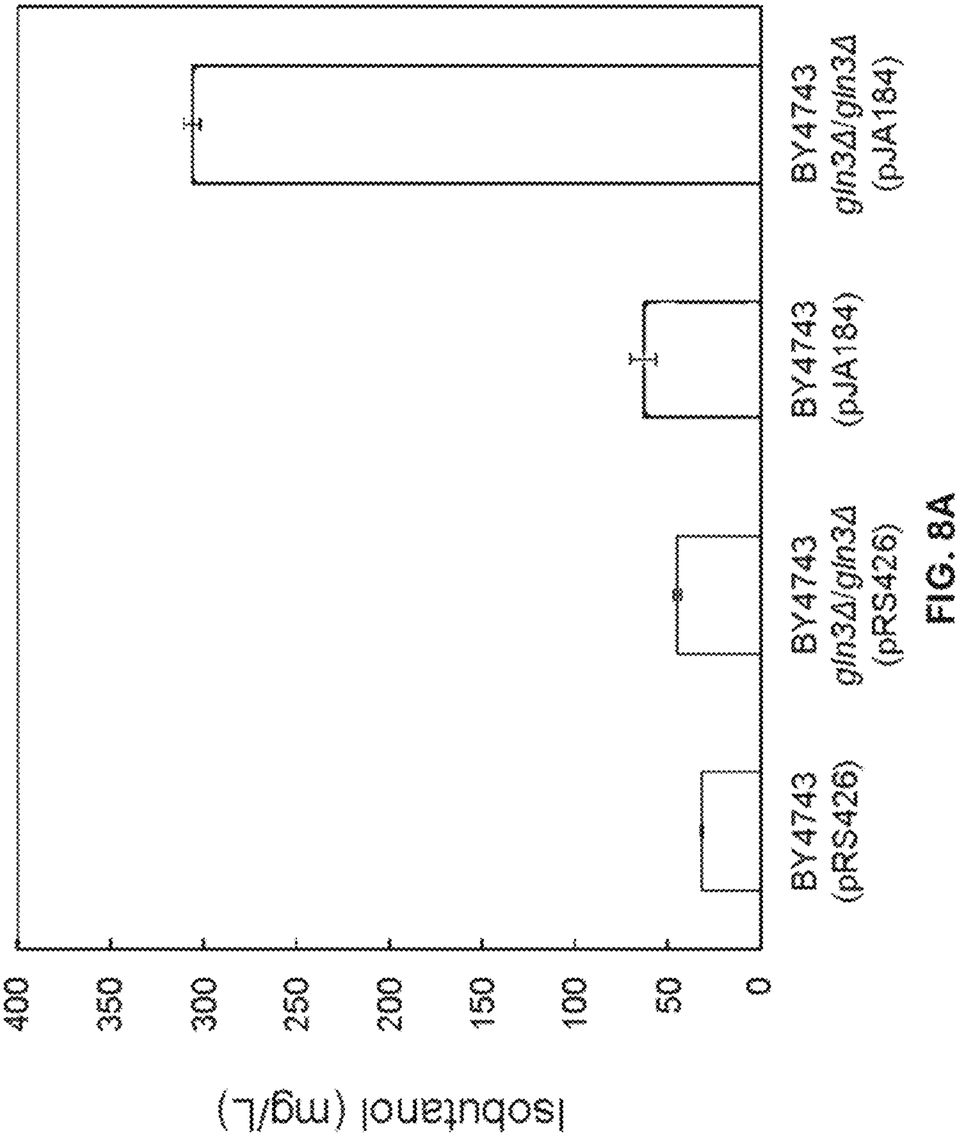
FIG. 8A is a graph showing isobutanol production of the homozygous BY4743 gln3Δ/gln3Δ strain in inhouse-prepared SC-Ura medium compared to wild type BY4743, either harboring an empty 2μ plasmid (pRS426) or harboring a 2μ plasmid overexpressing the five enzymes responsible for converting pyruvate to isobutanol in their natural locations (pJA184).

Example 5: Isobutanol Production is Significantly Increased in the Hypertolerant Gln3Δ Strain Enhancing isobutanol tolerance in a strain engineered to produce isobutanol could boost production. To test this possibility, five genes were overexpressed in the isobutanol biosynthetic pathway, ILV2, ILV3, ILV5, and ADH7 (from *S. cerevisiae*) and KDC (from *Lactococcus lactis*) in the gln3Δ strain in their native locations (mitochondria and cytosol) or targeted exclusively to the mitochondria, which significantly increases isobutanol titers. The native or mitochondrial isobutanol biosynthetic pathways were introduced into a gln3Δ/gln3Δ homozygous diploid BY4743 strain using a 2μ plasmid and compared isobutanol production to equivalent strains constructed in the wild type background. Homozygous deletion of GLN3 and overexpression of the isobutanol biosynthetic enzymes in their native locations (mitochondria and cytosol) using constitutive promoters (pJA184) enhances isobutanol production 4.9-fold relative to BY4743 harboring the same plasmid (pJA184), from 63±7 mg/L in the wild type, to 306±4 mg/L (FIG. 8A). Deletion of GLN3 enhances isobutanol production in engineered BY4743 strains in both commercial (FIG. 8A) and inhouse prepared (FIG. 8B) media. See Table 1, below.

TABLE 1 concentrations of components in media

| Components | Commercial Medium Final Concentration (mg/L) | Inhouse Medium Final Concentration (mg/L) |
|---|---|---|
| Adenine | 18 | 95 |
| p-Aminobenzoic acid | 8 | 9.5 |
| Ammonium sulfate | 5000 | 5000 |
| Alanine | 76 | 95 |
| Argiine | 76 | 95 |
| Asparagine | 76 | 95 |
| Aspartic acid | 76 | 95 |
| Cysteine | 76 | 95 |
| Glutamic acid | 76 | 95 |
| Glutamine | 76 | 95 |
| Glycine | 76 | 95 |
| Histidine | 76 | 95 |
| Inositol | 76 | 95 |
| Isoleucine | 76 | 95 |
| Leucine | 380 | 190 |
| Lysine | 76 | 95 |
| Methionine | 76 | 95 |
| Phenylalanine | 76 | 95 |
| Proline | 76 | 95 |
| Serine | 76 | 95 |
| Theonine | 76 | 95 |
| Tryptophan | 76 | 95 |
| Tyrosine | 76 | 95 |
| Uracil | 76 | 95 |
| Valine | 76 | 95 |
| Yeast nitrogen base without amino acids | 1700 | 1500 |

Figure 9:
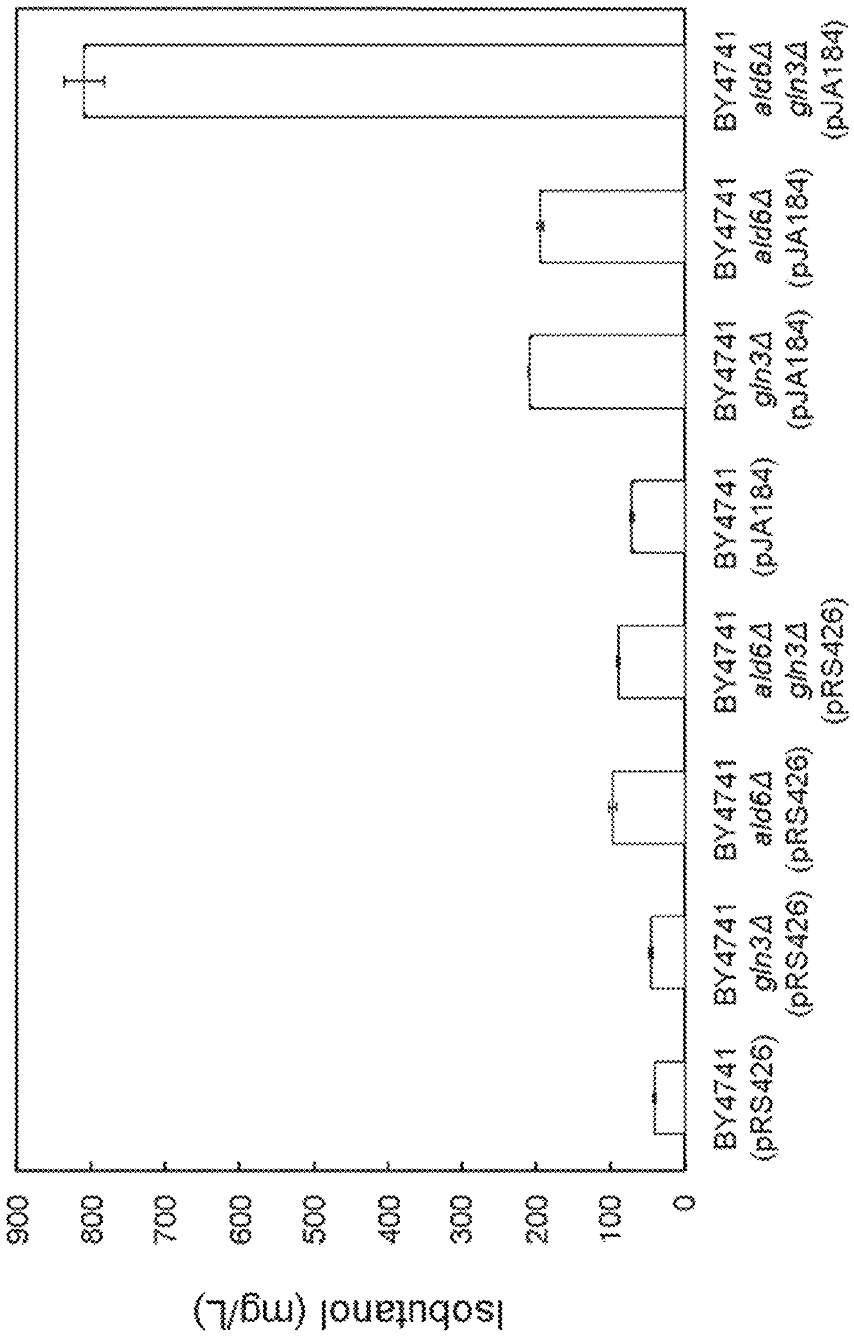
FIG. 9 is a graph illustrating the effects of GLN3 and ALD6 deletions on isobutanol production of the haploid BY4741 strain, compared to wild type BY4741, either harboring an empty 2μ plasmid (pRS426) or harboring a 2μ plasmid overexpressing the five enzymes responsible for converting pyruvate to isobutanol in their natural locations (pJA184).

While isobutanol titers did not improve in strains harboring the mitochondrial pathway, the effect of the GLN3 deletion is preserved in haploid strains overexpressing the natively-localized isobutanol pathway. The BY4741 gln3Δ strain harboring pJA184 exhibits a 2.9-fold increase in titers compared to the wild type BY4741 harboring the same plasmid (FIG. 9). Additional deletion of ALD6, which boosts isobutanol titers, acts synergistically with the GLN3 deletion to further increase isobutanol production. The gln3Δ ald6Δ strain harboring pJA184 achieves an isobutanol titer of 809±27 mg/L, representing a 4.1-fold improvement over the ald6Δ strain and an 11.3-fold increase in isobutanol production over the wild type strain harboring the same plasmid (FIG. 9). These results suggest that enhancing isobutanol tolerance by deleting GLN3 is a useful strategy for improving isobutanol titers in engineered yeast strains.

Similar results are expected when different heavy alcohols and pathways are used.

Enhancement of branched-chain alcohol production in yeast requires not only increasing productivity, but also improving yeast tolerance to their toxic effects. Some genes, such as those involved in tryptophan biosynthesis and vacuolar function, are important for general cell tolerance to both simple alcohols (methanol, ethanol) and higher alcohols. On the other hand, genes encoding for enzymes in the PPP are important for tolerance specifically to isobutanol and other higher alcohols (C4-C6), without influencing tolerance to ethanol.

Deletion of GLN3 is the single most impactful deletion for enhancing yeast tolerance to isobutanol (FIG. 6). The fact that the enhanced tolerance of the gln3Δ strain is specific to branched-chain alcohols, having no effect on tolerance to ethanol or higher linear alcohols (FIG. 7), suggests that the toxicity caused by isobutanol and other branched-chain alcohols has a unique mechanism of action, and that branched-chain alcohols induce a specific adaptive response in yeast. When nitrogen sources are scarce, yeast resort to utilizing their own amino acids as a nitrogen source, including branched-chain amino acids. This process involves the Ehrlich degradation pathway, which converts valine, leucine, and isoleucine to isobutanol, isopentanol, and 2-methyl-1-butanol, respectively, after they have been deaminated. Therefore, yeast has evolved to sense these fusel alcohols, which are branched but not linear or simple (ethanol or methanol), as a signal for nitrogen starvation. Consistent with this adaptive trait, when the wild type strain is grown in the presence of isobutanol, our transcriptomic data shows that the cells respond as if they were starving for nitrogen, even though they are growing in SC medium, rich with amino acids and ammonium sulfate (See Table 1). The isobutanol-induced nitrogen starvation response we observe is two-pronged: on one hand, the cell induces many genes involved in amino acid biosynthesis and transport of nitrogen sources, including amino acids; on the other hand, the cell represses glycolysis, and genes involved in cell wall biogenesis and membrane lipid biosynthesis.

Figure 10A:
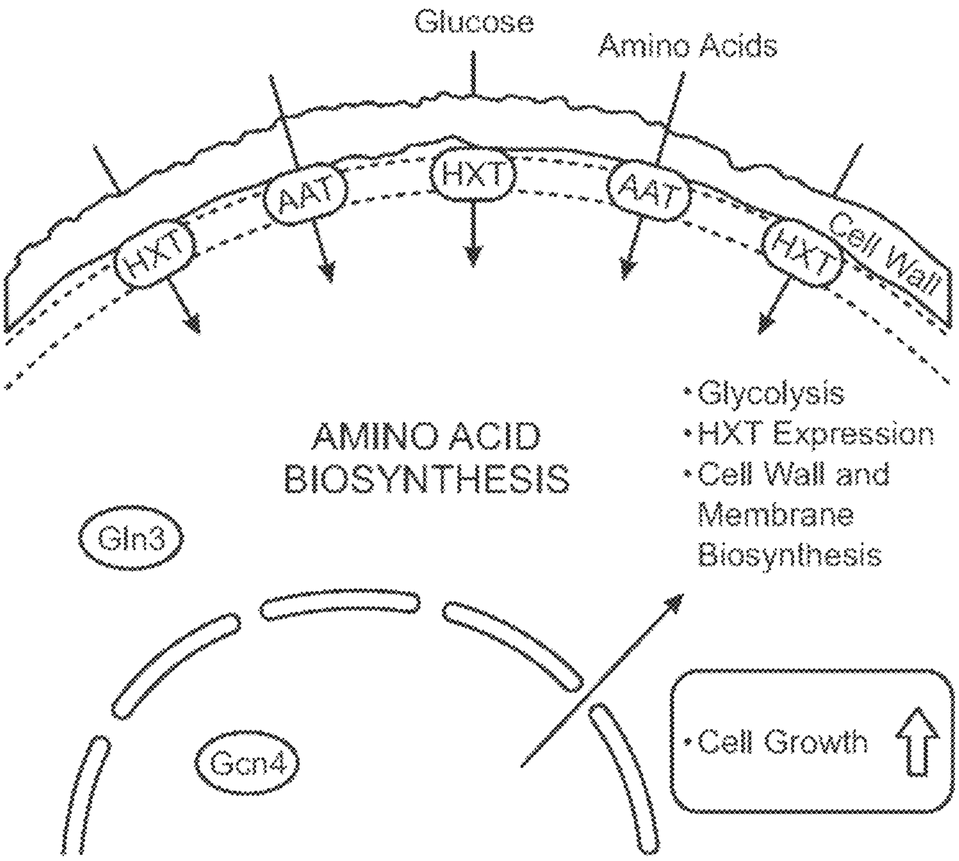
FIG. 10A is a schematic model of the behavior of wild type or gln3Δ strains grown in nitrogen-rich conditions without isobutanol (or other heavy alcohols) in the media. Glucose and amino acids are imported into the cell via hexose transporters (HXT) and amino acid transporters (AAT), respectively. Glycolysis, cell wall biogenesis, and membrane lipid biosynthesis are prioritized.
Figure 10B:
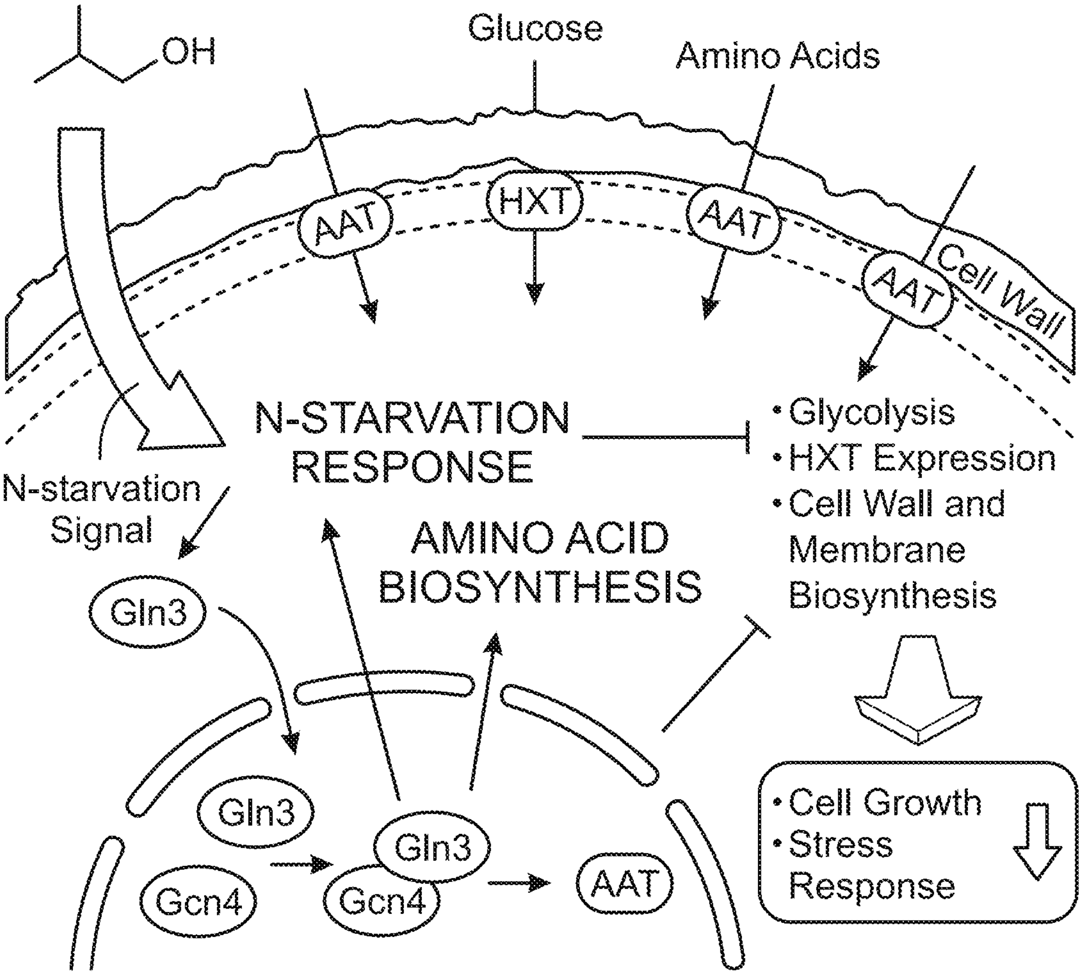
FIG. 10B is a schematic model of the natural response of wild type cells to extracellular isobutanol (or other heavy alcohol) stress. Heavy alcohols such as isobutanol trigger a nitrogen starvation response, causing the transcription factor Gln3p to enter the nucleus. Gln3p forms a complex with transcription factor Gcn4p, which together activate transcription of genes involved in amino acid biosynthesis and import. Gln3p may also strengthen the nitrogen starvation response, causing downregulation of glycolytic genes, and genes involved in hexose import, cell wall biogenesis, and membrane lipid biosynthesis. As a result, cell growth and the cell's ability to respond to isobutanol (IbOH) or other heavy alcohol stress are repressed.

It is expected that isobutanol and other heavy alcohols induce a nitrogen starvation response, resulting in reduced transcription of glycolytic genes is consistent with the observation that the vacuolar proteinase Pep4p is downregulated in wild type cells grown with isobutanol. It was recently shown that deletion of Pep4p under nitrogen starvation conditions reduces transcription and post-translational modification of glycolytic enzymes. This response of wild type cells is appropriate when cells are truly starving for nitrogen and exposed to sub-lethal concentrations of isobutanol in their environments, as evolution would favor cells that stop dividing (by repressing glycolysis as well as cell wall and membrane lipid biosynthesis) and shift their metabolism to prioritize amino acid biosynthesis and nitrogen conservation and assimilation (FIGS. 10A and 10B). However, when cells face isobutanol concentrations in fermentations designed to produce this alcohol, the natural nitrogen starvation response is counterproductive. Not only do the cells waste energy and resources producing and scavenging for amino acids they do not need, but they also take these resources away from processes necessary to divide and withstand high isobutanol concentrations.

This mechanism of heavy alcohol toxicity is consistent with the finding that deletion of GLN3 significantly enhances yeast tolerance to branched-chain alcohols. GLN3 encodes a transcription factor that activates several genes that are repressed when cells have access to high-quality nitrogen sources, such as glutamine, asparagine, or ammonia. Under such conditions, Gln3p is phosphorylated and sequestered in the cytosol by Ure2p, which prevents Gln3p from activating its target genes. When the cell has access to only low quality nitrogen sources, such as proline or urea, or senses nitrogen starvation, the Tor1p-containing TOR Complex 1 (TORC1) releases its repression over the Tap42-Sit4 and Tap42-PP2A complexes, which in turn dephosphorylate Gln3p, allowing it to dissociate from Ure2p, enter the nucleus, and initiate the nitrogen starvation response.

Figure 10C:
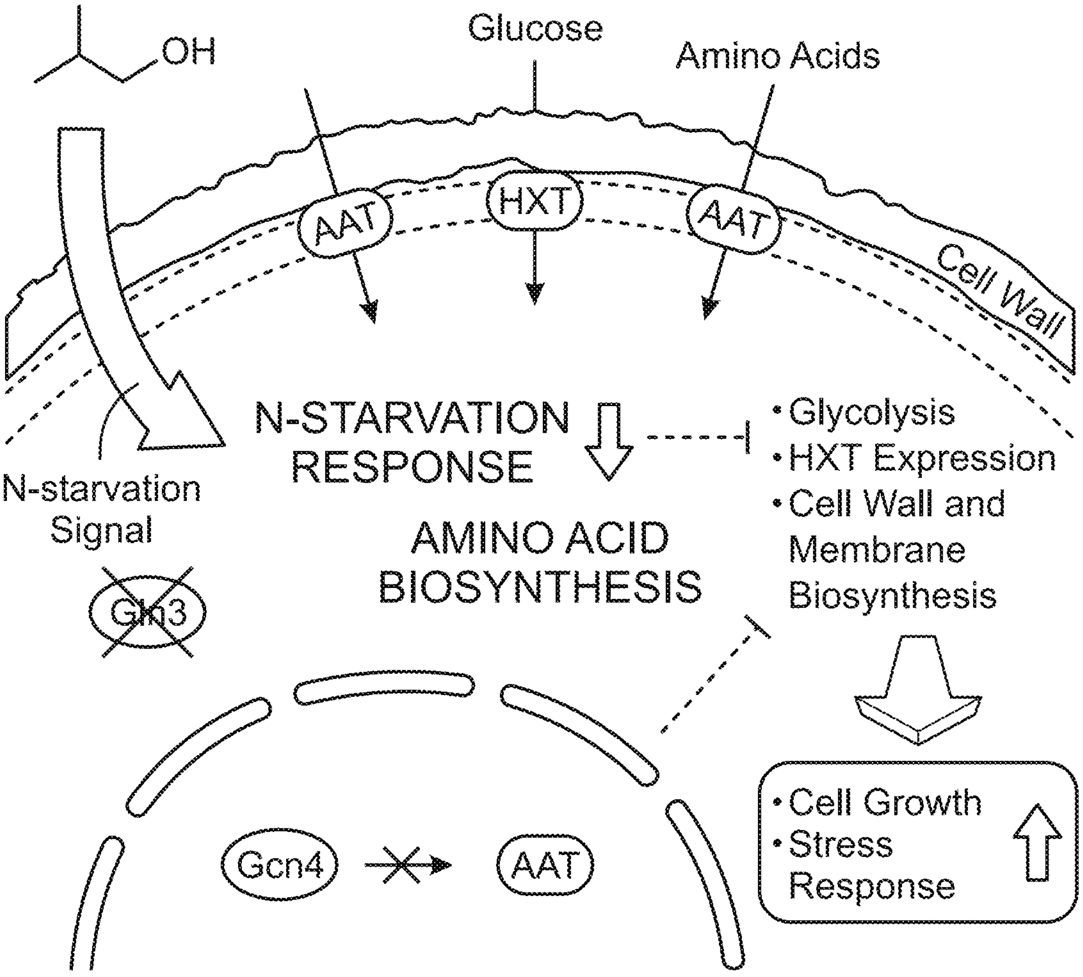
FIG. 10C is a schematic model of the response of gln3Δ strains to extracellular isobutanol (or other heavy alcohol) stress. Disruption of the function of GLN3 evades the natural nitrogen starvation response to enhance tolerance and growth in isobutanol. Without GLN3, genes involved in glycolysis, cell wall biogenesis, and membrane lipid biosynthesis are upregulated, while those involved in amino acid biosynthesis and import are downregulated compared to the wild type strain grown in the same conditions. As a result, cell growth and the IbOH stress response (and/or other heavy alcohol stress response) are more active. Expression of HXT genes is unchanged between the wild type and gln3Δ strains grown with isobutanol or other heavy alcohol. Other disclosed disruption strains have similar response models.

Thus, when GLN3 is disrupted, this signaling pathway is interrupted, and the nitrogen starvation response fails to implement. As a result, the gln3Δ strain does not waste resources needlessly synthesizing amino acids or scavenging for nitrogen; it instead keeps glycolysis active, affording the cell more energy to affront isobutanol toxicity, as well as other processes required for cell division (FIG. 10C). This mechanism is also consistent with the observation that deletion of GLN3 enhances tolerance to branched-chain alcohols, but not to linear or simple alcohols, as only the former would be recognized as degradation products of amino acids, initiating a nitrogen starvation signal to which GLN3 has evolved to respond.

The genomic and transcriptomic data suggest that isobutanol activates GCN4, allowing Gln3p to induce its target genes. Disruption of GCN4, or its activator GCN3, result in strains with enhanced tolerance to 1.4% isobutanol—with TFs of 0.86 and 0.98, respectively, compared to a TF of 0.38 for the wild type (See Table 2)—consistent with the role of Gcn4p in keeping Gln3p in the nucleus during nitrogen starvation.

TABLE 2

Tolerance factors of the wild type BY4741 strain in various concentrations of isobutanol and ethanol

| | Tolerance Factor(s) of the wild type BY4741 |
|---|---|
| Isobutanol (%) | |
| 0.6 | 0.92 |
| 1.2 | 0.72 |
| 1.4 | 0.38 |
| 1.5 | 0.19 |
| 1.6 | 0.11 |
| Ethanol (%) | |
| 8.0 | 0.31 |

Furthermore, multiple genes regulated by GCN4 are down-regulated in the gln3Δ strain grown with isobutanol compared to the wild type strain with isobutanol. Although GLN3 is not directly transcriptionally regulated by Gcn4p, it has been shown that a Gln3-Gcn4 protein complex forms in response to nitrogen starvation, which focuses the transcriptional response of Gcn4p to genes regulated by Gln3p. The results suggest that the genes regulated by Gcn4p that are differentially expressed in the wild type and gln3Δ strains in the presence of isobutanol are controlled by this Gln3-Gcn4 protein complex, expanding the list of known genes regulated by GLN3 and offering an additional explanation for the enhanced isobutanol tolerance of the gcn4Δ strain.

Figure 11A:
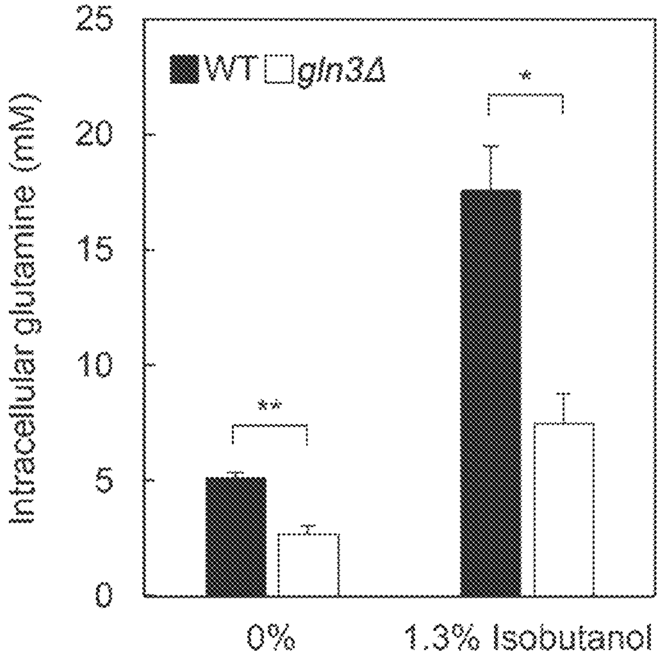
FIG. 11A is a graph of the concentration of glutamine in the metabolites extracted from cells of wild type and gln3Δ strains where the cells were grown in SC medium with or without 1.3% (v/v) isobutanol at 30° C. for 12 h.
Figure 11B:
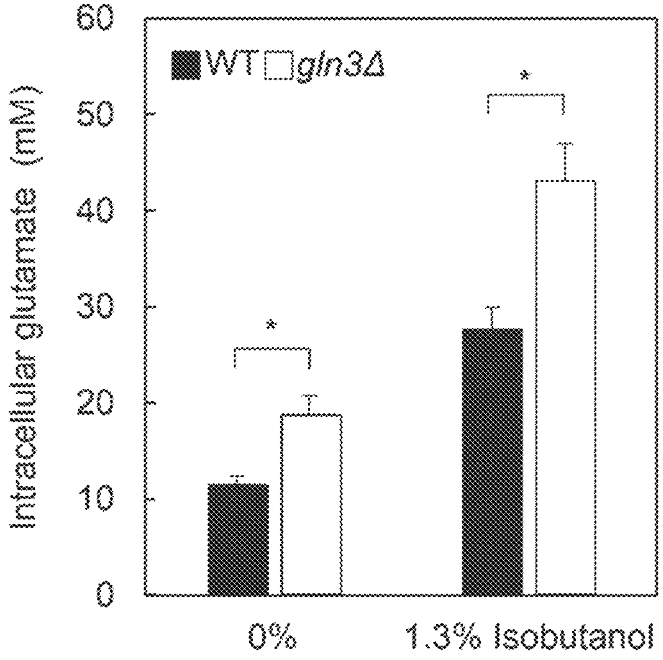
FIG. 11B is a graph of the concentration of glutamate in the metabolites extracted from cells of wild type and gln3Δ strains where the cells were grown in SC medium with or without 1.3% (v/v) isobutanol at 30° C. for 12 h.

Measurements of intracellular amino acid concentrations also support a mechanism wherein the enhanced isobutanol tolerance of gln3Δ strains is linked to amino acid metabolism. GLN3 regulates intracellular levels of glutamine and glutamate, which serve as nitrogen donors, and are typically the amino acids with the highest intracellular concentrations. GLN1, a target gene of Gln3p, encodes an enzyme involved in biosynthesis of glutamine from glutamate. Consistent with its regulation by Gln3p, GLN1 is downregulated in the gln3Δ strain relative to the wild type in both the absence and presence of isobutanol. Furthermore, previous results showed that inhibition of GLN1 causes depletion of intracellular glutamine. Thus, it is likely that downregulation of GLN1 is the cause of the decreases in intracellular glutamine levels and increases in intracellular glutamate levels we observe upon the deletion of GLN3 in both media conditions (FIGS. 11A and 11B).

Figure 8B:
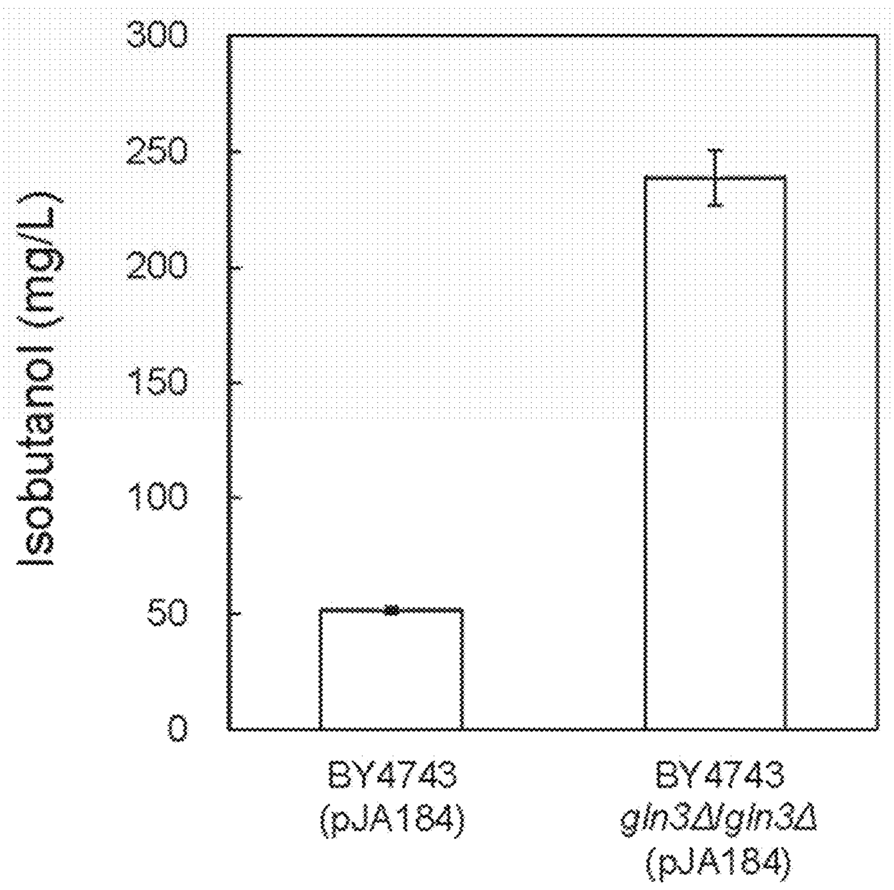
FIG. 8B is a graph showing isobutanol production of the homozygous BY4743 gln3Δ/gln3Δ strain in inhouse-prepared SC-Ura medium compared to wild type BY4743, harboring a 2μ plasmid overexpressing the five enzymes responsible for converting pyruvate to isobutanol in their natural locations (pJA184).

The adaptive response of yeast to isobutanol, which the cell recognizes as a signal of nitrogen starvation, causes toxicity by inhibiting cell growth even before isobutanol inflicts physical damage to the cell. For this reason, disruption of this response by deleting GLN3 leads to a 4.04-fold increase in isobutanol tolerance compared to the wild type (FIG. 7). Furthermore, disruption of this adaptive mechanism can significantly boost isobutanol titers in strains engineered to produce it (FIGS. 8A and 8B).

In preferred embodiments, the enzymes for the heavy alcohol biosynthesis are localized in their natural compartments.

In preferred embodiments, the yeast strains are free of a mitochondrial pathway to produce the heavy alcohol.

The findings provide insights into the cellular response of yeast to heavy alcohols, and mechanisms underlying specific toxicity and tolerance to heavy alcohols (See FIGS. 10A-10C).

Construction of Complementation, Deletion, and Overexpression Strains

All primers used for strain construction are listed in Table 3.

For complementation of the trp1 auxotrophy in laboratory strains CEN.PK2-1C and SEY6210, a TRP1 DNA fragment containing its promoter, ORF, and terminator amplified from BY4741 genomic DNA by PCR using the primers TRP1-Pro-F and TRP1-Term-R was used to transform CEN.PK2-1C and SEY6210 wild type strains. Transformants carrying a functional TRP1 gene (CEN. PK2-1C TRP1 and SEY6210 TRP1) were selected on SD agar plates.

TABLE 3

Primers used in various embodiments

| Primer | Sequence (5'-3') | Target region or description |
|---|---|---|
| TRPI-Pro-F | ACACTGAGTAATGGTAGTTA TAAGAAAGAG [SEQ ID NO: 1] | $P_{TRP1}$-TRP1-$T_{TRP1}$ |
| TRPI-Term-R | TGGTGTTTATGCAAAGAAAC CACTGTGTTT [SEQ ID NO: 2] | |
| GLN3-F | TCTTGCAAGACAGAGAAAGA TGTTC [SEQ ID NO: 3] | 5' Flanking sequence of GLN3-KanMX4- |
| GLN3-D | AAACAAATAATACCAATGCT CAGGA [SEQ ID NO: 4] | 3' flanking sequence of GLN3 |
| GND1-A | TAAATCACCTGCTACCTCTCT GTTC [SEQ ID NO: 5] | 5' Flanking sequence of GND1-KanMX4- |
| GND1-D | TTTTCTGACTTCATGATTTTG TGTC [SEQ ID NO: 6] | 3' flanking sequence of GND1 |
| ZWF1-A | ATTATTAATGTGGGATTTTTG GCTC [SEQ ID NO: 7] | 5' Flanking sequence of ZWF1-KanMX4- |
| ZWF1-D | TCAATGATAAGTACAAGTCC AATCG [SEQ ID NO: 8] | 3' flanking sequence of ZWF1 |
| ALD6-KO-F | TCTTGTTTTATAGAAGAAAAA ACATCAAGAAACATCTTTAA CATACACAAACACATACTAT CAGAATACATACGCTGCAGG TCGACAACC [SEQ ID NO: 9] | 5' Flanking sequence of ALD6-KanMX4- 3' flanking sequence of ALD6 |
| ALD6-KO-R | GACGTAAGACCAAGTAAGTT TATATGAAAGTATTTTGTGTA TATGACGGAAAGAAATGCAG GTTGGTACACTAGTGGATCTG ATATCACC [SEQ ID NO: 10] | |
| GLN3-KO-F | ATAACAGAGTGTGTAAGAAA GAGAGACGAGAGAGAGCAC AGGGCCCCCTTTTCCCCCACC AACAAACAATACGCTGCAGG TCGACAACC [SEQ ID NO: 11] | 5' Flanking sequence of GLN3-NatMX6- 3' flanking sequence of GLN3 |
| GLN3-KO-R | GAAAATCTATCAATGCAACC GTTCAGTAATTATTAACATAA TAAGAATAATGATAATGATA ATACGCGGCTAGTGGATCTG ATATCACC [SEQ ID NO: 12] | |
| GLN3-F2 | TTTGCTCTATTACCCGGCGGA CAGG [SEQ ID NO: 13] | Forward primer annealing upstream of the introduced DNA fragment for GLN3 deletion |
| GND1-A2 | CCCTTCTACATAACTCCATGC ATGC [SEQ ID NO: 14] | Forward primer annealing upstream of the introduced DNA fragment for GND1 deletion |
| ZWF1-A2 | TGCTAAAAGCCCGGTTTCGG CTCGG [SEQ ID NO: 15] | Forward primer annealing upstream of the introduced DNA fragment for ZWF1 deletion |
| ALD6-F | GGGATTCAAGACAAGCAACC TTGTTAGTCA [SEQ ID NO: 16] | Forward primer annealing upstream of the introduced DNA fragment for ALD6 deletion |
| Jla_oli239 | ATTCGTCGTCGGGGAACACC [SEQ ID NO: 17] | Reverse primer annealing within NatMX6 |
| JW38 | GCACGTCAAGACTGTCAAGG [SEQ ID NO: 18] | Reverse primer annealing within KanMX4 |

Deletion strains reconstructed in BY4741 and CEN.PK2-1C TRP1 were generated using a PCR-based gene disruption method (Wach et al., 1994). Each of the target ORFs (e.g., GND1, ZWF1, and GLN3) were replaced by the kanMX4 gene. This was achieved by PCR amplifying DNA fragments consisting of the 5' flanking sequence of the ORF, the kanMX4 gene, and the 3' flanking sequence of the ORF from the genomic DNA of the corresponding BY4741 deletion strain (Euroscarf). BY4741 and CEN.PK2-1C TRP1 strains were transformed with the amplified DNA fragments and selected on YPD plates with the corresponding selective antibiotic. The gene deletions were confirmed by PCR with forward primers annealing upstream of the introduced DNA fragment and reverse primers annealing within the antibiotic resistance marker. Gene deletions in BY4741 isobutanol production strains were constructed and verified in a similar manner, except lox sites were added to the deletion cassettes, such that antibiotic resistance markers could be recovered if needed.

Thus, lox66-natMX6-lox71 cassette in pYZ84 (Hammer and Avalos, 2017) and loxP-kanMX4-loxP cassette in pUG6 (Gueldener et al., 2002) were PCR-amplified with 5' and 3' homology to GLN3 and ALD6, respectively (Tables S10 and S11). To overexpress PPP genes, 2μ plasmids harboring GND1, GND2, ZWF1, TKL1, TKL2, TAL1, SOL3, or RPE1, each under the control of their native promoters and terminators (Huang et al., 2013) (See FIG. 12), were introduced into the wild type BY4741 strain.

Media for Yeast Strains

For most screens and analyses of alcohol tolerance, wild type and deletion strains can be cultured in synthetic complete (SC) medium made inhouse (see Table 1) at 30° C., and 2% glucose. Strains overexpressing PPP genes can be cultured in SC medium lacking uracil (SC-Ura) made inhouse. For isobutanol production experiments, strains can be fermented in 0.67% (w/v) yeast nitrogen base without amino acids, 0.192% (w/v) of a commercially available SC-Ura medium supplement (Sigma-Aldrich, Y1501), as well as media made inhouse, both containing 15% (w/v) glucose. Transformants complemented with TRP1 can be selected on agar plates with minimal synthetic defined (SD) medium [0.67% (w/v) yeast nitrogen base without amino acids, 2% (w/v) glucose, 0.5% (w/v) casamino acids, 0.002% (w/v) adenine, 0.002% (w/v) L-histidine, 0.012% (w/v) L-leucine, and 0.002% (w/v) uracil]. Transformants with open reading frame (ORF) deletions generated by insertion of the kanMX4 or natMX6 markers can be selected on YPD [1% (w/v) yeast extract, 2% (w/v) Bacto peptone, and 2% (w/v) glucose] agar plates containing 200 μg/mL G418 (Nacalai Tesque, Kyoto, Japan) or 200 μg/mL Nourseothricin (Werner BioAgents, Jena, Germany), respectively. Transformants harboring 2μ plasmids to overexpress a single PPP gene under the control of its native promoter can be selected on SC-Ura agar plates. Yeast transformations can be performed using a standard lithium acetate method (Ito et al., 1983).

Construction of Isobutanol-Producing Yeast Strains

After deletion of, e.g., ALD6 and/or GLN3, the five genes in the biosynthetic pathway from pyruvate to isobutanol were overexpressed in a single 2μ plasmid. The 2μ plasmid introduced, pJA184 (Avalos et al., 2013), contains ILV2, ILV3, ILV5, with their gene products targeted to mitochondria; and an α-ketoacid decarboxylase (KDC) from *Lactococcus lactis* (LlKivD) and an alcohol dehydrogenase (ADH7), with their gene products targeted to the cytosol. Wild type and isobutanol-tolerant strains were transformed with either plasmid pJA184 for expression of the five genes in their natural compartments, or empty plasmid pRS426 (Christianson et al., 1992) as a negative control. Transformants were isolated on SC-Ura agar plates incubated at 30° C. for 2 to 4 d. Because a wide range of colony sizes, growth rates, and isobutanol productivity can result from 2μ plasmid transformations, 8-12 colonies from each transformation were screened to identify those producing the most isobutanol.

Fermentations for Isobutanol Production

Single colonies from the transformations were cultured in 5 mL of SC-Ura medium in 14 mL round-bottom falcon tubes (Corning, NY, USA) at 30° C. for 24 h, followed by centrifugation at 2,000×g for 3 min. Cell pellets were re-suspended in 5 mL of SC-Ura medium containing 10% (w/v) glucose and cultured under semi-aerobic conditions at 30° C. with 250 rpm agitation for 24 h. After measuring the $OD_{600}$ of each culture, cells were recovered by centrifugation for 3 min at 2,000×g and re-suspended in SC-Ura medium containing 15% (w/v) glucose to obtain a starting $OD_{600}$ of 15. After transferring 5 mL of each diluted culture to a new 14 mL round-bottom tube, fermentations were carried out under semi-aerobic conditions at 30° C. with 250 rpm agitation for 24 h.

Quantitative Determination of Isobutanol Production

Concentrations of isobutanol in the supernatant after 24 h fermentations were measured by high-performance liquid chromatography (HPLC). Cell cultures were centrifuged at 12,000×g and 4° C. for 2 min, and the supernatant was filtered through Ultrafree-MC centrifugal filter units (0.45 μm; Millipore, Bedford, MA, USA). Filtered supernatant (200 L) was analyzed using an HPLC system consisting of a pump (LC-20AD, Shimadzu, Kyoto, Japan), autosampler (SIL-20A, Shimadzu), degasser (DGU-14A, Shimadzu), column oven (CTO-20A, Shimadzu), refractive index (RI) detector (RID-10A, Shimadzu), and Aminex HPX-87H column (Bio-Rad, Hercules, CA, USA). The column was eluted with 5 mM H2SO4 at a flow rate of 0.6 mL/min and 55° C. To determine the isobutanol concentration in each sample, peak areas from the chromatographic data, monitored by the RI detector, were compared to those of freshly prepared isobutanol standards using LC Solution software (Shimadzu).

TABLE 4

Additional Examples of other deletion strains that have or are expected to have increased heavy alcohol production as compared to wild type strains.

| Example # | Description |
|---|---|
| 6 | avt3Δ |
| 7 | avt3Δ prr2Δ |
| 8 | avt3Δ sfk1Δ ssp120Δ ydr134cΔ ydr514cΔ |
| 9 | avt3Δ vps55Δ asn2Δ avt7Δ |
| 10 | gcn3Δ |
| 11 | gcn3Δ sfk1Δ ssp120Δ |
| 12 | gcn3Δ ydr391cΔ ylr225cΔ tpl197cΔ |
| 13 | gcn3Δ yrl236cΔ ylr278cΔ ylr279wΔ ylr280cΔ |
| 14 | gln3Δ |
| 15 | gln3Δ |
| 16 | gln3Δ aro80Δ |
| 17 | gln3Δ cyb2Δ ddc1Δ ecm25Δ ktr7Δ thi4Δ mrs4Δ |
| 18 | gln3Δ ecm25Δ ktr7Δ thi4Δ mrs4Δ |
| 19 | gln3Δ vps55Δ |
| 20 | gln3Δ vps55Δ gnp1Δ |
| 21 | gln3Δ vps55Δ gnp1Δ act3Δ |
| 22 | gln3Δ vps55Δ gnp1Δ act3Δ gcn3Δ |
| 23 | gln3Δ vps55Δ gnp1Δ act3Δ gcn3Δ ydr391cΔ |
| 24 | gnp1Δ |
| 25 | gnp1Δ isn1Δ ist3Δ pdc5Δ |
| 26 | gnp1Δ stb6Δ ubi4Δ |

TABLE 4-continued

Additional Examples of other deletion strains that have or are expected to have increased heavy alcohol production as compared to wild type strains.

| Example # | Description |
|---|---|
| 27 | gnp3Δ gcm2Δ |
| 28 | gnp3Δ gcm2Δ isn1Δ ist3Δ |
| 29 | vps55Δ |
| 30 | ydr391cΔ |
| 31 | ydr391cΔ ygr016wΔ yil024cΔ ykl147cΔ |

Construction and Fermentation of 2-Phenylethanol-Producing Yeast Strains

Improving de novo production of 2-phenylethanol in *S. cerevisiae* can begin as described in Hassing, et al., 2019, by modifying the central carbon metabolism to optimize supply of erythose-4-phosphate (E4P) and phosphoenolpyruvate (PEP) to the shikimate pathway, combined with the overexpression and mutations alleviating allosteric regulation of genes of the shikimate and Ehrlich pathways. From there, as presently disclosed, the production of 2-phenylethanol can be further improved via deletion of genes that disrupt the natural nitrogen starvation response, e.g., VPS55, using methods known to those of skill in the art. The strains can be cultured in, e.g., a 2 L batch bioreactor with 20 g/L glucose at a fixed pH of 5.0.

Construction and Fermentation of Isopentanol-Producing Yeast Strains

Production of isopentanol can be achieved by overexpressing the leucine biosynthetic enzymes encoded by LEU4, LEU1, and LEU2 (REF). Alternatively, compartmentalized overexpression of the same enzymes (encoded by LEU4, LEU1, and LEU2) in mitochondria of an isobutanol production strain of *S. cerevisiae* leads to increased isopentanol production (Hammer, et al., 2020). Those strains can be further modified as presently disclosed by introducing a missense mutation, such that instead of (e.g., the gln3 gene) encoding for its normal phenylalanine in (codons TTT/TTC) the disrupted gene encodes for leucine (TTA/TTG). Alternatively, they can be modified by introducing a frameshift mutation, such that instead of (e.g., the gln3 gene) encoding, for example, the amino acids Asp, Asp with consecutive codons GAC GAC, a frame shift is caused by, for example, introducing an extra nucleotide to produce GAA CGA C resulting in a change in the encoded amino acid residues to Glu, Arg, and many subsequent amino acid substitutions. Those cells can then be grown overnight in 1 mL SC media containing 2% glucose, lacking other amino acids or nucleobases as needed.

Construction and Fermentation of 2-Methyl-1-Butanol Producing Yeast Strains

Compartmentalizing the five-gene isobutanol biosynthetic pathway in mitochondria of BAT1 deletion strains can improve 2-methyl-1-butanol production in *S. cerevisiae*, if valine is present in the fermentation media. (Hammer, et al., 2017). From there, as presently disclosed, the production of 2-methyl-1-butanol can be further improved via, e.g., disruption of the avt3 gene. This can be done by, e.g., introducing a non-sense mutation, such as replacing the cytosine in one of the triplets coding for glutamine with a thymine (that is, changing the codons from CAA or CAG to TAA or TAG, respectively) resulting in a Stop codon that causes an early termination of the protein encoded by the gene. Colonies isolated from transformations can be grown overnight at 30° C. in sterile well plates in 1 mL of SC medium lacking uracil supplemented with 2% glucose.

Other yeast species, such as *K. marxianus, O. polymorpha*, or *Y. lipolytica* can be engineered to overproduce branched-chain alcohols by overexpressing the same genes used to engineer this overproduction in *S. cerevisiae*. For example, overexpressing genes encoding for an acetolactate synthase (encoded in *S. cerevisiae* by ILV2), an acetohydroxyacid reductoisomerase (encoded in *S. cerevisiae* by ILV5), a dehydroxyacid dehydratase (encoded in *S. cerevisiae* by ILV3), a 2-ketoacid decarboxylase (encoded in *S. cerevisiae* by ARO10), and an alcohol dehydrogenase (encoded in *S. cerevisiae* by ADH genes), respectively, compartmentalized in either the cytosolic or mitochondrial compartments results in the overproduction of isobutanol and 2-methy-1-butanol. Additional overexpression of genes encoding for an alpha-isopropylmalate synthase (encoded in *S. cerevisiae* by LEU4), isopropylmalate isomerase (encoded in *S. cerevisiae* by LEU1) and beta-isopropylmalate dehydrogenase (encoded in *S. cerevisiae* by LEU2), respectively, compartmentalized in either the cytosolic or mitochondrial compartments results in the overproduction of isopentanol.

Those skilled in the art will recognize or be able to ascertain using no more than routine experimentation many equivalents to the specific embodiments of the invention described herein. Such equivalents are intended to be encompassed by the following claims.

What is claimed:

1. A method for producing at least one heavy alcohol, comprising:

providing a heavy alcohol production system comprising:

an engineered yeast strain having a biosynthetic pathway configured to produce at least one heavy alcohol, wherein the engineered yeast strain has a disruption of GLN3, VPS55, and/or AVT3 as compared to a corresponding wild-type yeast strain, wherein the engineered yeast strain has an increase in the production of the at least one heavy alcohol over the corresponding wild-type yeast strain, as measured using titers of the at least one heavy alcohol;

forming a cell culture by fermenting the engineered yeast strain in conditions that enable the expression of the at least one heavy alcohol; and allowing the engineered yeast strain to produce a larger quantity of the at least one alcohol than can be produced by the corresponding wild-type strain, wherein the at least one heavy alcohol includes 2-butanol, tert-Butanol, 1-Pentanol, and 2-Methyl-1-butanol, isobutanol, and/or isopentanol for GLN3 disruption strains, 2-phenylethanol for VPS55 disruption strains, and 2-methyl-1-butanol for AVT3 disruption strains.

2. The method according to claim 1, further comprising producing a filtered supernatant by separating and filtering the cell culture.

3. The method according to claim 2, wherein separating the cell culture is accomplished via sedimentation, centrifugation, filtration, or a combination thereof.

4. The method according to claim 2, further comprising analyzing the filtered supernatant to determine the production of the at least one heavy alcohol.

5. The method according to claim 1, wherein the at least one heavy alcohol comprises a branched chain alcohol.

* * * * *

SEQUENCE LISTING

```
<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: Primer: TRPI-Pro-F

<400> SEQUENCE: 1

acactgagta atggtagtta taagaaagag                                   30


<210> SEQ ID NO 2
<211> LENGTH: 30
<212> TYPE: DNA
<213> ORGANISM: Artificial Sequence
<220> FEATURE:
```

<223> OTHER INFORMATION: Primer: TRPI-Term-R

<400> SEQUENCE: 2
tggtgtttat gcaaagaaac cactgtgttt 30

<210> SEQ ID NO 3
<211> LENGTH: 25
<212> TYPE: DNA
<213> ORGANISM: Artificial Sequence
<220> FEATURE:
<223> OTHER INFORMATION: Primer: GLN3-F

<400> SEQUENCE: 3
tcttgcaaga cagagaaaga tgttc 25

<210> SEQ ID NO 4
<211> LENGTH: 25
<212> TYPE: DNA
<213> ORGANISM: Artificial Sequence
<220> FEATURE:
<223> OTHER INFORMATION: Primer: GLN3-D

<400> SEQUENCE: 4
aaacaaataa taccaatgct cagga 25

<210> SEQ ID NO 5
<211> LENGTH: 25
<212> TYPE: DNA
<213> ORGANISM: Artificial Sequence
<220> FEATURE:
<223> OTHER INFORMATION: Primer: GND1-A

<400> SEQUENCE: 5
taaatcacct gctacctctc tgttc 25

<210> SEQ ID NO 6
<211> LENGTH: 25
<212> TYPE: DNA
<213> ORGANISM: Artificial Sequence
<220> FEATURE:
<223> OTHER INFORMATION: Primer: GND1-D

<400> SEQUENCE: 6
ttttctgact tcatgatttt gtgtc 25

<210> SEQ ID NO 7
<211> LENGTH: 25
<212> TYPE: DNA
<213> ORGANISM: Artificial Sequence
<220> FEATURE:
<223> OTHER INFORMATION: Primer: ZWF1-A

<400> SEQUENCE: 7
attattaatg tgggattttt ggctc 25

<210> SEQ ID NO 8
<211> LENGTH: 25
<212> TYPE: DNA
<213> ORGANISM: Artificial Sequence
<220> FEATURE:
<223> OTHER INFORMATION: Primer: ZWF1-D

<400> SEQUENCE: 8
tcaatgataa gtacaagtcc aatcg 25

<210> SEQ ID NO 9
<211> LENGTH: 90
<212> TYPE: DNA
<213> ORGANISM: Artificial Sequence
<220> FEATURE:
<223> OTHER INFORMATION: Primer: ALD6-KO-F

<400> SEQUENCE: 9
tcttgtttta tagaagaaaa aacatcaaga aacatcttta acatacacaa acacatacta 60
tcagaataca tacgctgcag gtcgacaacc 90

<210> SEQ ID NO 10
<211> LENGTH: 90
<212> TYPE: DNA
<213> ORGANISM: Artificial Sequence
<220> FEATURE:
<223> OTHER INFORMATION: Primer: ALD6-KO-R

<400> SEQUENCE: 10
gacgtaagac caagtaagtt tatatgaaag tattttgtgt atatgacgga aagaaatgca 60
ggttggtaca ctagtggatc tgatatcacc 90

<210> SEQ ID NO 11
<211> LENGTH: 89
<212> TYPE: DNA
<213> ORGANISM: Artificial Sequence
<220> FEATURE:
<223> OTHER INFORMATION: Primer: GLN3-KO-F

<400> SEQUENCE: 11
ataacagagt gtgtaagaaa gagagacgag agagagcaca gggccccctt ttcccccacc 60
aacaaacaat acgctgcagg tcgacaacc 89

<210> SEQ ID NO 12
<211> LENGTH: 89
<212> TYPE: DNA
<213> ORGANISM: Artificial Sequence
<220> FEATURE:
<223> OTHER INFORMATION: Primer: GLN3-KO-R

<400> SEQUENCE: 12
gaaaatctat caatgcaacc gttcagtaat tattaacata ataagaataa tgataatgat 60
aatacgcggc tagtggatct gatatcacc 89

<210> SEQ ID NO 13
<211> LENGTH: 25
<212> TYPE: DNA
<213> ORGANISM: Artificial Sequence
<220> FEATURE:
<223> OTHER INFORMATION: Primer: GLN3-F2

<400> SEQUENCE: 13
tttgctctat tacccggcgg acagg 25

<210> SEQ ID NO 14
<211> LENGTH: 25
<212> TYPE: DNA
<213> ORGANISM: Artificial Sequence
<220> FEATURE:
<223> OTHER INFORMATION: Primer: GND1-A2

<400> SEQUENCE: 14
cccttctaca taactccatg catgc 25

-continued

```
<210> SEQ ID NO 15
<211> LENGTH: 25
<212> TYPE: DNA
<213> ORGANISM: Artificial Sequence
<220> FEATURE:
<223> OTHER INFORMATION: Primer: ZWF1-A2

<400> SEQUENCE: 15

tgctaaaagc ccggtttcgg ctcgg                                           25


<210> SEQ ID NO 16
<211> LENGTH: 30
<212> TYPE: DNA
<213> ORGANISM: Artificial Sequence
<220> FEATURE:
<223> OTHER INFORMATION: Primer: ALD6-F

<400> SEQUENCE: 16

gggattcaag acaagcaacc ttgttagtca                                      30


<210> SEQ ID NO 17
<211> LENGTH: 20
<212> TYPE: DNA
<213> ORGANISM: Artificial Sequence
<220> FEATURE:
<223> OTHER INFORMATION: Primer: Jla_oli239

<400> SEQUENCE: 17

attcgtcgtc ggggaacacc                                                 20


<210> SEQ ID NO 18
<211> LENGTH: 20
<212> TYPE: DNA
<213> ORGANISM: Artificial Sequence
<220> FEATURE:
<223> OTHER INFORMATION: Primer: JW38

<400> SEQUENCE: 18

gcacgtcaag actgtcaagg                                                 20
```